(12) United States Patent
Semsar et al.

(10) Patent No.: US 12,295,705 B2
(45) Date of Patent: May 13, 2025

(54) ARTIFICIAL INTELLIGENCE-BASED ROBOTIC SYSTEM FOR PHYSICAL THERAPY

(71) Applicant: AR & NS Investment, LLC, Newport Coast, CA (US)

(72) Inventors: Neda Semsar, Newport Coast, CA (US); Arman Rofougaran, Newport Coast, CA (US)

(73) Assignee: AR & NS Investment, LLC, Newport Coast, CA (US)

( * ) Notice: Subject to any disclaimer, the term of this patent is extended or adjusted under 35 U.S.C. 154(b) by 0 days.

(21) Appl. No.: 18/390,933

(22) Filed: Dec. 20, 2023

(65) Prior Publication Data
US 2024/0122483 A1 Apr. 18, 2024

Related U.S. Application Data

(62) Division of application No. 16/556,924, filed on Aug. 30, 2019, now Pat. No. 11,903,679.

(51) Int. Cl.
*B25J 11/00* (2006.01)
*A61B 5/01* (2006.01)
*G06N 5/043* (2023.01)
*G06N 20/00* (2019.01)
*G06V 10/776* (2022.01)
(Continued)

(52) U.S. Cl.
CPC .............. *A61B 5/01* (2013.01); *B25J 11/009* (2013.01); *G06N 5/043* (2013.01); *G06N 20/00* (2019.01); *G06V 10/776* (2022.01); *G06V 10/82* (2022.01); *G06V 40/174* (2022.01); *G06V 40/176* (2022.01)

(58) Field of Classification Search
CPC ..................................................... B25J 11/009
See application file for complete search history.

(56) References Cited

U.S. PATENT DOCUMENTS 10,376,203 B2    8/2019   Dullen
10,758,150 B2 *  9/2020   Saroka ................. A61B 5/00
(Continued)

FOREIGN PATENT DOCUMENTS

AU    2014249335 A1     10/2015
WO    WO-2020246946 A1 * 12/2020 ............ G06Q 50/22

OTHER PUBLICATIONS

Jiang F, et al. Artificial intelligence in healthcare: past, present and future, Stroke and Vascular Neurology, Jun. 22, 2017. (Year: 2017).*
(Continued)

*Primary Examiner* — Kurtis Gills
(74) *Attorney, Agent, or Firm* — CHIP LAW GROUP

(57) ABSTRACT

A robotic system includes retrieval of a priori stimulus based on an input that indicates a current health state and a target health state of a user. A set of test stimuli specific for the user is determined and a stimulus device is controlled to provide the set of test stimuli to the user. A set of responses discernible on the body of the user is determined, and a set of stimulus parameters for the stimulus device is calibrated based on the combination of the set of responses, the current health state, the target health state, and a trained AI-based system. A new stimulus is applied to a portion of the body of the user that shifts a condition of the user from the current health state towards the target health state.

14 Claims, 9 Drawing Sheets

(51) Int. Cl.
*G06V 10/82* (2022.01)
*G06V 40/16* (2022.01)

(56) References Cited

U.S. PATENT DOCUMENTS

| | | | | |
|---|---|---|---|---|
| 2013/0282117 | A1* | 10/2013 | Van Heugten | A61F 2/14 |
| | | | | 623/6.22 |
| 2018/0289279 | A1 | 10/2018 | Ren et al. | |
| 2019/0065970 | A1* | 2/2019 | Bonutti | G16H 20/10 |
| 2019/0111255 | A1* | 4/2019 | Errico | A61N 2/02 |
| 2019/0172571 | A1 | 6/2019 | Ramaci | |
| 2019/0175909 | A1 | 6/2019 | Wagner et al. | |
| 2019/0180851 | A1 | 6/2019 | Simhon et al. | |
| 2019/0183450 | A1* | 6/2019 | Binotto | G16H 50/30 |
| 2019/0189259 | A1* | 6/2019 | Clark | G16H 10/60 |
| 2019/0221303 | A1 | 7/2019 | Bennett | |
| 2020/0337888 | A1* | 10/2020 | Beer | A61B 5/0004 |

OTHER PUBLICATIONS

Final Office Action for U.S. Appl. No. 16/556,924 dated Jan. 24, 2023.
Jiang et al., Artificial Intelligence in healthcare: past, present and future, Stroke and Vascular Neurology, pp. 230-243, 2017.
Jiang et al., Artificial intelligence in healthcare: past, present, and future, Stroke and Vascular Neurology, Jun. 22, 2017, 14 pages.
Non-Final Office Action for U.S. Appl. No. 16/556,924 dated Jun. 21, 2023.
Notice of Allowance for U.S. Appl. No. 16/556,924 dated Aug. 25, 2022.
Notice of Allowance for U.S. Appl. No. 16/556,924 dated Oct. 20, 2023.

* cited by examiner

ARTIFICIAL INTELLIGENCE-BASED ROBOTIC SYSTEM FOR PHYSICAL THERAPY

CROSS-REFERENCE TO RELATED APPLICATIONS/INCORPORATION BY REFERENCE

This Patent Application makes reference to, claims priority to, claims the benefit of, and is a Divisional Application of U.S. patent application Ser. No. 16/556,924 filed on Aug. 30, 2019.

FIELD OF TECHNOLOGY

Certain embodiments of the disclosure relate to health maintenance systems and technologies. More specifically, certain embodiments of the disclosure relate to an artificial intelligence-based robotic system for physical therapy.

BACKGROUND

Congenital or acquired musculoskeletal system disorders and diseases affecting the musculoskeletal system are one of the major health problems affecting people. Physical therapy and rehabilitation are one of the most common treatment performed for restoring deficiencies observed in the musculoskeletal system of people due to congenital disorders, injuries, diseases, or aging. Physical therapy and rehabilitation include healing patients by means of controlled electrical current, hot or cold application, controlled pressure application, and/or exercises.

Generally, physical therapy is carried out under the supervision of specialist doctors and therapists in physical therapy and rehabilitation centers with a variety of instruments and devices. Moreover, quality of health services still largely depends on the experience and competence of the specialist doctors and therapists. In the current model of practicing medicine, these specialist doctors and therapists use trial and error method to find the right physical therapy for a patient. Moreover, during a physical therapy session, a human specialist doctor or therapist may only be able to guide a patient through a handful of movements and track a very significant movement as progress. In such a scenario, minor responses of the patient may go unnoticed by the human specialist doctor or therapist. In addition to this, the number of instruments and devices and specialist doctors and therapists is not sufficient to meet the increasing need for physical therapy. Due to insufficient resources, efficient health care service may not be provided to people in need. In light of the foregoing, there exists a need for a technical solution that solves the abovementioned problems and enables provisioning of physical therapy to patients in an efficient manner.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY OF THE DISCLOSURE

An artificial intelligence-based robotic system is provided for physical therapy, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION OF THE DISCLOSURE

Certain embodiments of the disclosure may be found in an Artificial Intelligence (AI)-based robotic system for physical therapy. There are various therapies that affect physical or biological processes of the body. Examples include but are not limited to, medications, diet control, physical therapy, or stress management. Multiple therapeutic modalities (or approaches), such as physiological, behavior al, social, may be used either in conjunction with medicines or without medicines for human well-being and health, and to control biological-based disorder. Typically, when human beings exercise or undergo physical therapy, that makes them feel good, the body releases certain chemicals, for example, endorphins. These endorphins interact with the receptors in the human brain that reduce the perception of pain. Endorphins also trigger a positive feeling in the body, similar to that of medicines that are used to reduce/control pain and stress, which may help in treating various medical conditions.

The AI-based robotic system is able to provide physical therapy, which may be used specifically for an individual or for a group therapy. Such physical therapy may result in improving a current health state of a user and achieving a target health state. The AI-based robotic system provides a technology that has the potential to become an alternative form of treatment for diseases without the need of taking medicines or at least complement and improve the existing model by reducing the usage and dosage of medicines, and thereby avoiding or reducing the side effects of medicines. The AI-based robotic system is highly receptive to various responses generated in a body of a user due to the provisioning of physical therapy and is capable of adjusting the physical therapy as per the responses generated. Further, the AI-based robotic system is able to provide quantifiable feedback on the progress and performance of the user. In the following description, reference is made to the accompanying drawings, which form a part hereof, and in which is shown, by way of illustration, various embodiments of the present disclosure.

Figure 1:
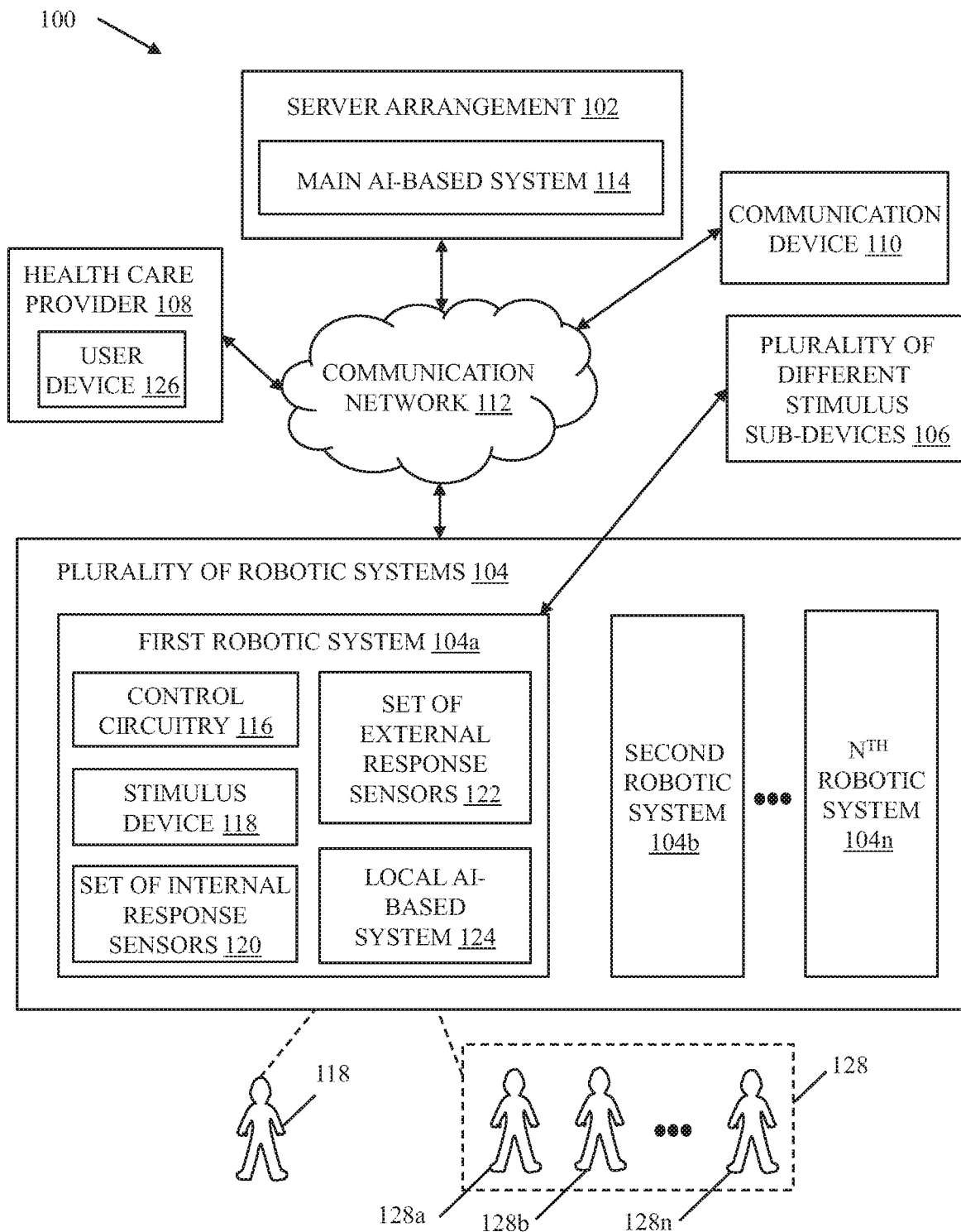
FIG. 1 is a block diagram that illustrates an exemplary environment of a health maintenance system with robotic systems for providing physical therapy to users, in accordance with an exemplary embodiment of the disclosure.

FIG. 1 is a block diagram that illustrates an exemplary environment of a health maintenance system with robotic systems for provisioning physical therapy, in accordance with an exemplary embodiment of the disclosure. With reference to FIG. 1, there is shown an exemplary network environment of a health maintenance system 100. The health maintenance system 100 includes a server arrangement 102, a plurality of robotic systems 104, a plurality of different stimulus sub-devices 106, a health care provider 108, a communication device 110, and a communication network 112.

The server arrangement (server system) 102 may include a main Artificial Intelligence (AI)-based system 114. The plurality of robotic systems 104 may include multiple robotic systems, such as a first robotic system 104a, a second robotic system 104b, and the like. The first robotic system 104a may include control circuitry 116, a stimulus device 118, a set of internal response sensors 120, a set of external response sensors 122, and a local AI-based system 124. It will be apparent to those of skill in the art that the other robotic systems 104b, . . . , 104n are functionally similar to the first robotic system 104a. A plurality of test users 128a, 128b, . . . , 128n and a target user 130 may be associated with the plurality of robotic systems 104. Hereinafter, the plurality of test users 128a, 128b, . . . , 128n are collectively referred to and designated as "the plurality of test users 128". Various devices in the network environment of the health maintenance system 100 may be communicatively coupled with each other via the communication network 112.

The server arrangement 102 includes suitable circuitry, interfaces, and/or logic configured to instruct the plurality of robotic systems 104 to provide a plurality of stimuli on various body portions of the plurality of test users 128. The server arrangement 102 is further configured to instruct the plurality of robotic systems 104 to sense and measure levels of a plurality of responses generated in the body portions of the plurality of test users 128 due to the application of the plurality of stimuli on the body portions of the plurality of test users 128. The server arrangement 102 is further configured to receive primary information pertaining to a plurality of stimulus-response pairs from the plurality of robotic systems 104, based on the measurement of the plurality of responses. The server arrangement 102 is further configured to receive, from the plurality of robotic systems 104, supplementary information associated with the plurality of test users 128 on which the plurality of stimuli was applied. The server arrangement 102 may be configured to convert the primary information and the supplementary information into an AI-based system-readable data format. Examples of the server arrangement 102 may include, but are not limited to, an application server, a cloud server, a web server, a database server, a mainframe server, or a combination thereof. Further, it should be appreciated that the server arrangement 102 may be a single hardware server or a plurality of hardware servers operating in a parallel or distributed architecture.

For the sake of brevity, operations of each of the plurality of robotic systems 104 are explained with respect to the first robotic system 104a. The first robotic system 104a includes the local AI-based system 124 that is communicatively coupled to the main AI-based system 114. The first robotic system 104a includes suitable logic, circuitry, and/or interfaces configured to provide physical therapy to the plurality of test users 128 and the target user 130. In some embodiments, the first robotic system 104a may be configured to receive control instructions, in online mode, from the server arrangement 102 to provide physical therapy to the plurality of test users 128 and the target user 130. In some embodiments, the first robotic system 104a may be configured to provide physical therapy to the plurality of test users 128 and the target user 130 on its own, in absence of online connectively or when an offline mode is set at the first robotic system 104a.

Figure 2:
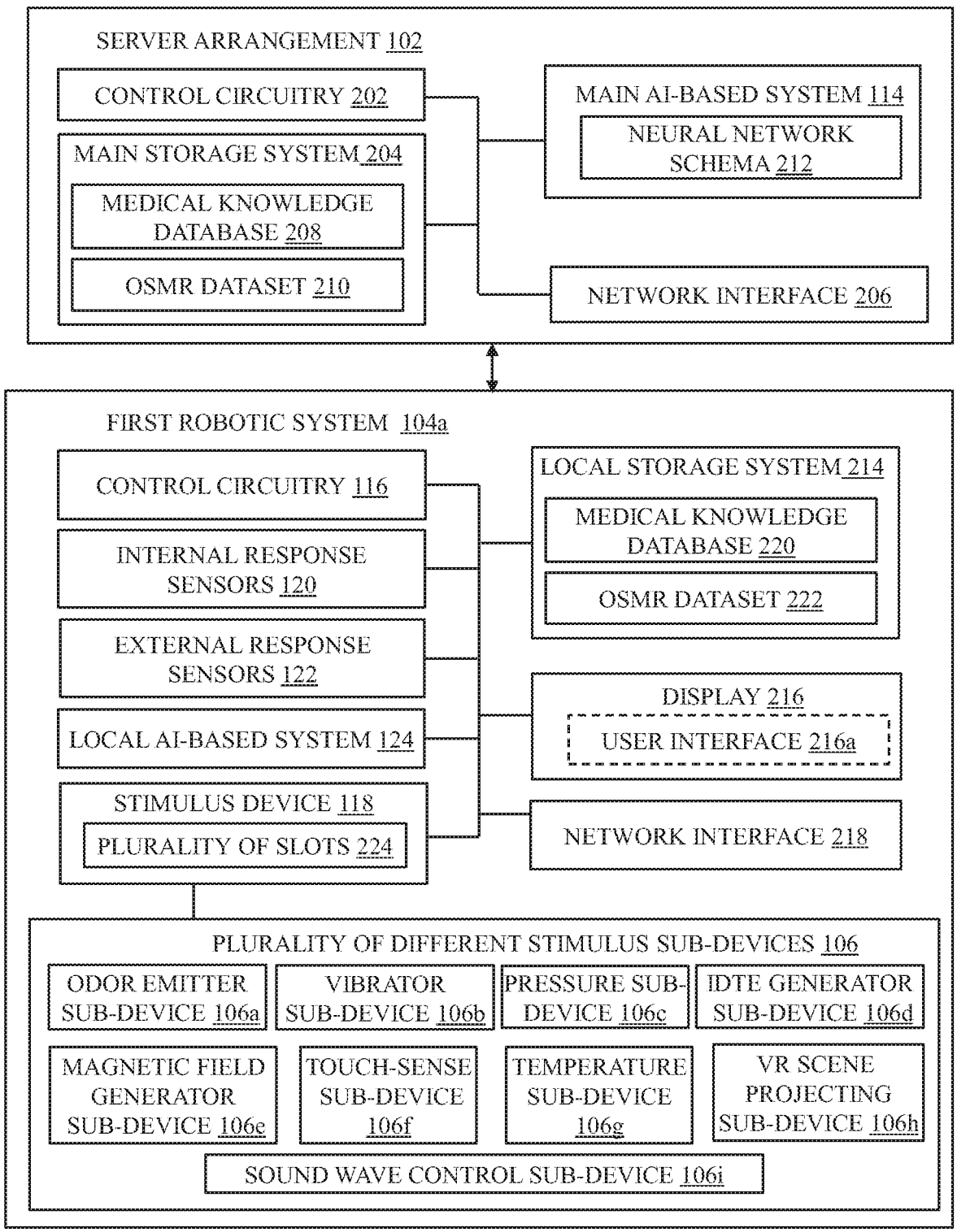
FIG. 2 illustrates different components of a server arrangement and a robotic system of FIG. 1, in accordance with an exemplary embodiment of the disclosure.

The plurality of different stimulus sub-devices 106 may correspond to modular attachments that may be attached to any of the plurality of robotic systems 104, for example, the first robotic system 104a, for applying different types of stimuli to the plurality of test users 128 and the target user 130. Each of the plurality of different stimulus sub-devices 106 may include suitable logic, circuitry, and/or interfaces configured to generate a stimulus such as a pressure stimulus, a temperature-based stimulus, a vibration stimulus, a sound wave stimulus, a virtual reality (VR) stimulus, an odor stimulus, a touch-based stimulus, and a magnetic stimulus. Examples of the plurality of different stimulus sub-devices 106 are shown in FIG. 2. In an implementation, the plurality of different stimulus sub-devices 106 may further include a phase array antenna component configured to generate ultrasound, magnetic, or a radio frequency (RF) in a specific frequency range or a combination thereof to monitor internal organs of a user (e.g. the plurality of test users 128a, 128b, . . . , 128n as well the target user 130).

The health care provider 108 may be an individual, institution, or agency that provides health services to health care consumers. For example, a physician, nurse, dentist, mental health worker, birth control counselor, and the like, may be considered the individual that provides the health care. The institution or agency may be a hospital, a clinic, a diagnostic center, or a genetic screening laboratory or any entity that provides health care to users. The user device 126 may be associated with the health care provider 108. Examples of the user device 126 may include, but is not limited to a smartphone, a human machine interface (HMI), a handheld device, a consumer electronic device, and other computing device. In some embodiments, the user device 126 may be a part of a machine, for example, a medical equipment.

The communication device 110 may correspond to a telecommunication hardware (e.g. a relay node or a repeater device). Examples of the communication device 110 may include, but are not limited to a 5G-capable repeater device, an Evolved-universal terrestrial radio access-New radio Dual Connectivity (EN-DC) device, a New Radio (NR)-enabled device, or a mmWave-enabled telecommunication device. The communication device 110 may facilitate communication in both sub 30 gigahertz to above 30 gigahertz. In one example, the communication device 110 may receive/transmit the RF signals from/to a base station or from another network node. In an implementation, in addition to the plurality of different stimulus sub-devices 106 (or instead of the plurality of different stimulus sub-devices 106), the communication device 110 may include a phase array antenna component configured to generate ultrasound, magnetic, or a radio frequency (RF) in a specific frequency range or a combination thereof to monitor internal organs of a given user (e.g. the plurality of test users 128a, 128b, . . . , 128n as well the target user 130). The communication device 110 may have a dual functionality of a fixed wireless access (FWA) for 4G/5G communication as well as heath monitoring functionality to monitor internal organs of the given user.

The communication network 112 may include a medium through which the various devices in the network environment, such as the server arrangement 102, the plurality of robotic systems 104, the health care provider 108, the communication device 110, and the user device 126, may communicate with each other. In some embodiments, a secured and dedicated communication channel may be established between the plurality of robotic systems 104 and the server arrangement 102. The communication network 112 may be implemented by use of various wired and wireless communication protocols. Examples of such wired and wireless communication protocols may include, but are not limited to, at least one of a Transmission Control Protocol and Internet Protocol (TCP/IP), User Datagram Protocol (UDP), Hypertext Transfer Protocol (HTTP), File Transfer Protocol (FTP), ZigBee, EDGE, IEEE 802.11, light fidelity (Li-Fi), 802.16, IEEE 802.11s, IEEE 802.11g, multi-hop communication, wireless access point (AP), device to device communication, cellular communication protocols, or Bluetooth (BT) communication protocols, or a combination thereof. Other examples of the communication network 112 may include, but are not limited to, the Internet, a cloud network, a Long Term Evolution (LTE) network, a secured Wireless Local Area Network (WLAN), a Local Area Network (LAN), a telephone line (POTS), or other wired or wireless network.

The main AI-based system 114 includes suitable circuitry, interfaces, and/or logic configured to train one or more neural network models, for example, recurrent neural network (RNN), such as Long Short Term Memory networks (LSTM) networks, convolution neural network (CNN), deep neural network (DNN), or an artificial neural network that may be a combination of the RNN and CNN networks. For example, the main AI-based system 114 may train the one or more neural network models to find a relationship between the plurality of stimuli and the plurality of responses generated in the body portions of the plurality of test users 128. In accordance with an embodiment, the trained model(s) is then deployed in one or more components of each of the plurality of robotic systems 104, for example, the local AI-based system 124. The deployed pre-trained neural network model(s) is remotely updatable as and when required. In some embodiments, the server arrangement 102 may establish a dedicated and secured link, via the communication network 112 or by use of the communication device 110 (e.g. a 5G enabled repeater device) to update various programmable components, such as the deployed pre-trained neural network model, of the plurality of robotic systems 104. In an embodiment, the main AI-based system 114 may employ supervised or unsupervised learning model. The main AI-based system 114 may employ machine learning algorithms, such as supervised, unsupervised, semi-supervised, or reinforcement machine learning algorithms for operation thereof. Typically, the machine learning algorithms refer to a category of algorithms employed by a system that allows the system to become more accurate in predicting outcomes and/or performing tasks, without being explicitly programmed.

The control circuitry 116 comprises suitable logic, circuitry, and interfaces configured to control the stimulus device 118 for providing the plurality of stimuli to the plurality of test users 128 for physical therapy. The control circuitry 116 is configured to process sensor data acquired from the set of internal response sensors 120 and the set of external response sensors 122. The control circuitry 116 is configured to control stimulus parameters for the stimulus device 118. Examples of the control circuitry 116 include an Application-Specific Integrated Circuit (ASIC) processor, a Complex Instruction Set Computing (CISC) processor, a combination of a central processing unit (CPU) and a graphics processing unit (GPU), a microcontroller, and/or other hardware processors.

The stimulus device 118 may correspond to a human senses' stimulator device. The stimulus device 118 may comprise suitable logic, circuitry, and/or interfaces configured to applying the plurality of stimuli to the body portions of the plurality of test users 128 for physical therapy. Examples of the plurality of stimuli may include, but are not limited to, calibrated pressure, calibrated vibration input, calibrated electric input, sound waves, magnetic input, a combination of physical therapy and virtual reality output, and/or hot and cold application. The stimulus device 118 may operate under the control of the control circuitry 116. In accordance with an embodiment, the stimulus device 118 may include various stimulus sub-devices for providing different types of stimuli to different body portions of a user. In accordance with another embodiment, the stimulus device 118 may include a plurality of slots (as shown in FIG. 2) to detachably attach the plurality of different stimulus sub-devices 106 in the plurality of slots in a modular arrangement.

The set of internal response sensors 120 includes suitable logic, circuitry, and/or interfaces configured to sense and measure a level of an internal response generated within a body of a user due to the application of a stimulus by the stimulus device 118. In accordance with an embodiment, the set of internal response sensors 120 may be attached to or placed on a body of a user (such as the plurality of test users 128 and the target user 130) in a non-invasive manner when the user is undergoing physical therapy by using the first robotic system 104*a*. Examples of the internal responses that may be sensed and measured by the set of internal response sensors 120 may include, but are not limited to, nerve conduction, neuron firing, activity in muscles or nerves, activity in different areas of brain, blood pressure, heart rate, breathing rate, body temperature, and/or pulse rate. In one example, the set of internal response sensors 120 may comprise an electromyograph for sensing and measuring activity in muscles and nerves. The set of internal response sensors 120 may further include a blood pressure monitor, a heart rate monitor, a pulse rate monitor, a temperature sensor, a low power magnetic resonance imaging system, and/or the like. The set of internal response sensors 120 may operate under the control of the control circuitry 116. In an implementation, the set of internal response sensors 120 may include one or more implantable chips to monitor internal response. In such implementation, the one or more implantable chips may be configured to cause chemical reaction or protein-mediation bioreactions within the body of a user (e.g. the plurality of test users 128*a*, 128*b*, . . . , 128*n* as well the target user 130) to derive a certain (or a specific) stimuli.

The set of external response sensors 122 includes suitable logic, circuitry, and/or interfaces configured to sense and measure a level of an external response discernible from external surface of the body of a user due to the application of a stimulus by the stimulus device 118. Examples of the external response that may be sensed and measured by the set of external response sensors 122 may include, but are not limited to, facial expressions, skin color, a body posture, gestures, and/or voice feedback. In one example, the set of external response sensors 122 may include an imaging device, a light detection and ranging (LiDAR) sensor, and/or a radio detection and ranging (RADAR) sensor for sensing changes in facial expressions and gestures of the user when stimulus is provided to the user. The set of external response sensors 122 may further include an audio sensor for sensing the voice feedback of the user when the stimulus is provided to the user. The set of external response sensors 122 may operate under the control of the control circuitry 116.

In operation, there may be a training phase and an operational phase of the health maintenance system 100. In the training phase, the server arrangement 102 may be configured to instruct the plurality of robotic systems 104, for example the first robotic system 104a, to provide the plurality of stimuli on various body portions of the plurality of test users 128. The plurality of test users 128 may be suffering from a plurality of congenital or acquired disorders and diseases affecting various systems of the body. The plurality of stimuli may include calibrated pressure, calibrated vibration input, calibrated electric input, calibrated magnetic input, hot and cold application, touch sense-based input, sound waves, and/or the like. The plurality of stimuli may further include presenting a VR-based digital therapeutic environment. The VR-based digital therapeutic environment may be a combination of audio effects and visual effects. Based on the instructions from the server arrangement 102, the control circuitry 116 may be configured to control the stimulus device 118 for providing the plurality of stimuli on various body portions of the plurality of test users 128. The stimulus device 118 may be configured to utilize the plurality of different stimulus sub-devices 106 for providing the plurality of stimuli on various body portions of the plurality of test users 128.

Each stimulus of the plurality of stimuli may generate a plurality of responses (for example, one or more internal responses and one or more external responses) in the body of the corresponding test user of the plurality of test users 128. Examples of the one or more internal responses may include, but are not limited to, nerve conduction, neuron firing, activity in muscles or nerves, activity in brain, alteration in blood pressure, and/or alteration in pulse rate. Examples of the one or more external responses that are discernible from external surface of the body of a test user may include, but are not limited to, change in facial expressions, change in gestures, a body posture, a change in skin color, and/or a voice feedback given by the test user. The server arrangement 102 may be further configured to instruct the plurality of robotic systems 104 to sense and measure levels of the one or more internal responses and the one or more external responses generated in the body portions of the plurality of test users 128 due to the application of the plurality of stimuli to the plurality of test users 128.

Based on the instructions from the server arrangement 102, the control circuitry 116 may be configured to control the set of internal response sensors 120 and the set of external response sensors 122 to sense and measure a level of each of the one or more internal responses and the one or more external responses generated due to the application of the plurality of stimuli. The set of internal response sensors 120 is configured to sense and measure the one or more internal responses generated within the body of the plurality of test users 128 due to the application of the plurality of stimuli by the stimulus device 118. The set of external response sensors 122 is configured to sense and measure the one or more external responses discernible on the body of the plurality of test users 128 due to the application of the plurality of stimuli by the stimulus device 118. The control circuitry 116 is configured to process sensor data generated by the set of internal response sensors 120 and the set of external response sensors 122 to determine the plurality of stimulus-response pairs.

Based on the processing of the sensor data, the plurality of robotic systems 104 may be configured to communicate the primary information pertaining to the determined plurality of stimulus-response pairs to the server arrangement 102. Each stimulus-response pair is indicative of a type of stimulus that was applied and a level of each response that was generated based on the applied stimulus. The plurality of robotic systems 104 may be further configured to communicate the supplementary information pertaining to the plurality of test users 128 to the server arrangement 102. The supplementary information of each test user 128a-128n may include details pertaining to physical characteristics, a feedback from a physical therapy expert, an age group, a geography, diagnostic information from at least one medical diagnosis test, a medical history, dosages of medicines prescribed for a current health state, and/or the like of the corresponding test user 128a to 128n. The server arrangement 102 may be further configured to convert the primary information and the supplementary information to a common format that may be easily read by the main AI-based system 114. For example, the AI-based system-readable data format may include patient information (e.g. patient unique identity), data and time information when the medical diagnosis test was conducted, a plurality of data fields, and corresponding measured values. The main AI-based system 114 may be configured to establish an associative relationship between each stimulus-response pair in the plurality of stimulus-response pairs with corresponding supplementary information. The main AI-based system 114 may be further configured to generate one-stimulus multi-response (OSMR) dataset (as shown in FIG. 2) based on the primary information and the supplementary information. In one exemplary scenario, the OSMR dataset may be a tabular database having a plurality of rows and columns. Each row may be associated with a single stimulus and may indicate the level of responses that were generated based on the corresponding single stimulus. The main AI-based system 114 may be configured to store the generated OSMR dataset in a memory associated with the server arrangement 102.

The main AI-based system 114 may be configured to determine a plurality of causes of similarity and variability in the plurality of responses based on the established associative relationship between each of the plurality of stimulus-response pairs and the corresponding supplementary information and available medical knowledge. Examples of the plurality of causes of similarity and variability determined by the main AI-based system 114 may include, but are not limited to, age groups, medicine intake, genomic, body weight, body mass index (BMI), ailment, or the like. The main AI-based system 114 may be further configured to segregate the generated OSMR dataset into a plurality of physical therapy categories, for example a first physical therapy category, a second physical therapy category, and a third physical therapy category. The first physical therapy category may include a first set of stimulus-response pairs that is suitable for a group therapy. For example, the first physical therapy category may include those stimuli that generated similar external and internal responses in a large number of test users. In other words, the first physical therapy category may be associated with generic stimuli that are suitable for all users. Similarly, the second physical therapy category may include a second set of stimulus-response pairs that is suitable for one or more specific traits, for example, age group, ailment, medical condition, and/or the like. The second set of stimulus-response pairs may be further segregated into sub-categories based on the one or more specific traits. Each sub-category may include a subset of the second set of stimulus-response pairs. For example, the second set of stimulus-response pairs may be segregated into two subsets such that the first subset of stimulus-response pairs is suitable for an age group of '25-30 years' and the second subset of stimulus-response pairs is suitable for users having lower back pain. Likewise, the third physical therapy category may include a third set of stimulus-response pairs that is suitable for specific users. The third set of stimulus-response pairs may be further segregated into subsets of stimulus-response pairs each personalized for a specific user. In accordance with an embodiment, the main AI-based system 114 may be configured to utilize supervised or unsupervised learning to find relationships among the plurality of stimulus-response pairs included in the OSMR dataset for segregating the OSMR dataset. Thus, all the stimulus-response pairs included in the OSMR dataset may be categorized and then sub-categorized and a learning may be derived. Based on the segregated OSMR dataset, the main AI-based system 114 is trained to generate a trained neural network model (i.e., the trained main AI-based system 114).

In the operational phase, the learnings of the trained main AI-based system 114 may be used to update the local AI-based system 124, by a transfer-learning operation from the trained main AI-based system 114 to the local AI-based system 124. For example, the segregated OSMR dataset may be communicated from the server arrangement 102 to each of the plurality of robotic systems 104 by the transfer-learning operation. In some embodiments, the trained main AI-based system 114 may be used for deployment into a new robotic system, such as the first robotic system 104a. The main AI-based system 114 may function as a main AI and the local AI-based system 124 may function as a local AI, which may be updated as and when required by the main AI-based system 114. The local AI-based system 124 may be computationally lighter (e.g. having a smaller number of hidden layers as compared to the main AI-based system 114).

In accordance with an embodiment, the target user 130 may be diagnosed with a medical condition, which may require physical therapy. In such a case, the health maintenance system 100 may be used to provide targeted physical therapy to the target user 130 for treating the medical condition. The health maintenance system 100 may be used as an alternative form of treating the medical condition without the need of taking medicines or at least reducing the intake or dosage of medicines.

In accordance with an embodiment, in the operational phase, the control circuitry 116 may be configured to receive user information (i.e., an input via a user interface) of the target user 130. The user information may include one or more details pertaining to a current health state of the target user 130, a target health state that is intended to be achieved for the target user 130, and supplementary information of the target user 130. The supplementary information of the target user 130 may include one or more details pertaining to physical characteristics of the target user 130, a geography, a feedback from a physical therapy expert, a first set of dosages of a first set of medicines prescribed for the current health state of the target user 130, and diagnostic information from at least one medical diagnosis test.

In accordance with an embodiment, the first robotic system 104a may operate in the offline mode. While in the offline mode, the control circuitry 116 may be configured to convert the received user information into an AI-based system-readable data format. Based on the converted user information, the local AI-based system 124 may be configured to retrieve a priori stimulus from a medical knowledge database. The local AI-based system 124 may be configured to determine a set of test stimuli specific for the target user 130 based on a combination of the retrieved priori stimulus and the user information of the target user 130. In one example, the priori stimulus may correspond to a stimulus that is recommended for treating at least one medical condition of the current health state of the target user 130. The local AI-based system 124 may provide, to the control circuitry 116, a first output that is indicative of one or more stimulus parameters and a first test duration for which the determined set of test stimuli may be applied to the target user 130. Based on the first output, the control circuitry 116 may be configured to activate the stimulus device 118 for providing the determined set of test stimuli to the target user 130 for the first test duration. In accordance with an embodiment, the control circuitry 116 may be configured to activate a single stimulus sub-device or a set of stimulus sub-devices from the plurality of different stimulus sub-devices 106 at a given timepoint in the first test duration for providing the determined set of test stimuli to the target user 130.

Due to the application of the determined set of test stimuli to the target user 130 for the first test duration, a first set of responses (i.e., internal responses) may be generated within the body of the target user 130 and a second set of responses (i.e., external responses) may be discernible from an external surface of the body of the target user 130. Under the control of the control circuitry 116, the set of internal response sensors 120 and the set of external response sensors 122 may be configured to sense and measure a level of each of the first set of responses and the second set of responses, respectively. The control circuitry 116 may be further configured to process sensor data acquired by the set of internal response sensors 120 and the set of external response sensors 122 pertaining to the first set of responses and the second set of responses, respectively.

Based on the processing of the sensor data acquired by the set of internal response sensors 120 pertaining to the first set of responses, the control circuitry 116 may be configured to identify a nerve that responds to at least one stimulus of the set of test stimuli, a muscle that responds to at least one stimulus of the set of test stimuli, or a change in an activity in a brain area of the target user 130, on the application of the set of test stimuli. The control circuitry 116 may be further configured to determine a modus operandi of the identified nerve, the identified muscle, or a pattern of the identified change in the activity in the brain area, on the application of each stimulus of the set of test stimuli. The control circuitry 116 may be further configured to quantify the level of response at the identified nerve, the identified muscle, or the pattern of the identified change in the activity in the brain area on application of each stimulus of the set of test stimuli based on the levels of responses measured by the set of internal response sensors 120. Based on the processing of the sensor data acquired by the set of external response sensors 122 pertaining to the second set of responses, the control circuitry 116 may be configured to identify a change in the facial expression, a pattern of facial expressions, a change in skin color, a body posture, a voice feedback from the target user 130, and a level of pain or comfort experienced by the target user 130, on a sequential application of the set of test stimuli on the target user 130 for the first test duration. The level of pain or comfort experienced by the target user 130 may be determined based on a deviation in a current user behavior from a baseline behavior of the target user 130.

The local AI-based system 124, under the control of the control circuitry 116, may be configured to determine a new stimulus having a set of stimulus parameters based on the combination of the first set of responses, the second set of responses, the current health state, and the target health state. The local AI-based system 124 may be configured to provide a second output to the control circuitry 116 based on the determination of the new stimulus. The second output may indicate the set of stimulus parameters, a second duration for which the new stimulus is to be applied to the target user 130, and one or more targeted body portions where the new stimulus is to be applied. The second duration for which the new stimulus is to be applied to the target user 130 may be greater than the first test duration. In an embodiment, the new stimulus may not be available during the training phase. In another embodiment, the new stimulus having the set of stimulus parameters is an existing stimulus that was available during the training phase.

Based on the second output from the local AI-based system 124, the control circuitry 116 may be configured to generate physical stimulation instructions pack specific for the target user 130. The control circuitry 116 may generate the physical stimulation instructions pack for calibrating the set of stimulus parameters for the stimulus device 118. The physical stimulation instructions pack may include a type of control signal for the plurality of different stimulus sub-devices 106, a time schedule, an intensity of output, and a set of sense identifiers. The time schedule may define a specific activation time and a specific duration to generate the new stimulus in the second duration by using one or more stimulus sub-devices of the plurality of different stimulus sub-devices 106 under the control of the stimulus device 118. Each sense identifier of the set of sense identifiers may indicate a unique specific sense stimulating item to be selected for output in accordance with the time schedule. For example, a first sense identifier may indicate a specific smell for output. In such a case, the intensity of output defines what amount of liquid or gas to be sprayed and in which direction. The stimulus device 118 may be configured to select a unique specific sense stimulating item (for example, an odor generating item, a visual effects item, an audio effects item, and a touch-sense based item) for generating a single or multiple sense stimulating output/s to stimulate a specific sense/s of a plurality of human senses based on the type of control signal included in the physical stimulation instructions pack. Thus, based on the physical stimulation instructions pack, the stimulus device 118 is re-configured with the calibrated set of stimulus parameters and the new stimulus is applied to at least targeted body portions of the target user 130.

The set of internal response sensors 120 and the set of external response sensors 122 may sense and measure a level of internal responses and external responses, respectively, generated in the body of the target user 130 due to the application of the new stimulus for the second duration. The internal responses and external responses generated in the body of the target user 130 due to the application of the new stimulus for the second duration may indicate that at least one condition of the target user 130 has shifted from the current health state towards the target health state. The local AI-based system 124 and the control circuitry 116 may continue to improve and personalize the stimulus applied to the target user 130 based the internal responses and the external responses exhibited by the target user 130 for achieving the target health state for the target user 130.

In accordance with an embodiment, the first robotic system 104a may operate in the online mode. While in the online mode, the first robotic system 104a may operate under the control of the server arrangement 102. Thus, based on the setting of the online mode at the first robotic system 104a, the main AI-based system 114 may be configured to execute the same operations as executed by the local AI-based system 124 in the offline mode. For example, the server arrangement 102 may receive the converted user information of the target user 130 from the control circuitry 116. The main AI-based system 114 may be configured to retrieve the priori stimulus from the medical knowledge database based on the received user information. The main AI-based system 114 may be configured to determine the set of test stimuli specific for the target user 130 based on the combination of the retrieved priori stimulus and the user information of the target user 130. The main AI-based system 114 may be configured to communicate the determined set of test stimuli to the local AI-based system 124 via the communication network 112. The local AI-based system 124 may provide, to the control circuitry 116, the first output and based on the first output the control circuitry 116 may be configured to activate the stimulus device 118 for providing the determined set of test stimuli to the target user 130 for the first test duration. Under the control of the control circuitry 116, the set of internal response sensors 120 and the set of external response sensors 122 may sense and measure the level of each of the first set of responses and the second set of responses, respectively. The sensor data acquired by the set of internal response sensors 120 and the set of external response sensors 122 pertaining to the first set of responses and the second set of responses, respectively, may be communicated to the server arrangement 102 by the control circuitry 116. The main AI-based system 114 may be configured to determine the new stimulus having the set of stimulus parameters based on the combination of the first set of responses, the second set of responses, the current health state, and the target health state. The main AI-based system 114 may be configured to generate the second output and communicate the second output to the local AI-based system 124 via the communication network 112. The local AI-based system 124 may then provide the second output to the control circuitry 116. The control circuitry 116 may then generate the physical stimulation instructions pack specific for the target user 130 and calibrate the set of stimulus parameters for the stimulus device 118. Thus, based on the physical stimulation instructions pack, the stimulus device 118 is re-configured with the calibrated set of stimulus parameters and the new stimulus is applied to at least targeted body portions of the target user 130. Due to the application of the new stimulus for the second duration, at least one condition of the target user 130 may shift from the current health state towards the target health state.

In accordance with an embodiment, the control circuitry 116 may be further configured to determine whether an alteration is required in the first set of dosages of the first set of medicines prescribed for the current health state of the target user 130, based on the application of the new stimulus to the body portion of the target user 130 and the shift in the at least one condition of the target user 130 from the current health state towards the target health state. The control circuitry 116 may be further configured to determine a second set of dosages for the first set of medicines that is different from the first set of dosages based on the determination that the alteration is required. The control circuitry 116 may be further configured to communicate a medicine dosage change recommendation report for the target user 130 to a prespecified user device (e.g. the user device 126) of the health care provider 108. The medicine dosage change recommendation report may include the second set of dosages for the first set of medicines and a plurality of health indicators related to the shift in the at least one condition of the target user 130 from the current health state towards the target health state. Such medicine dosage change recommendation report may assist a physician to make an informed decision to precisely reduce the first set of dosages of the first set of medicines approximately to the recommended second set of dosages.

In accordance with an embodiment, the trained plurality of robotic systems 104 may be deployed in a physical therapy center and may be operated by a dedicated health care operator (not shown). In such a scenario, the trained plurality of robotic systems 104 may cater to multiple target users, for example, the target user 130, who visit the physical therapy center. In another embodiment, the target user 130 may have purchased the trained first robotic system 104a from a service provider (not shown) for personal use.

In accordance with an embodiment, the health maintenance system 100 may have utility in sports field. For example, the trained first robotic system 104a may be utilized for improving a stamina of a sportsman. In such a scenario, the current health state defines the current stamina of the sports-person and the target health state defines the target stamina that is to be achieved. The local AI-based system 124, under the control of the main AI-based system 114, may be configured to determine the new stimulus, for example, new exercises, that intends to shift the current stamina of the sportsman towards the target stamina. The trained first robotic system 104a may detect the current health state of a sportsman, and continuously challenge his endurance, fitness, engagement, sports move, and the like, to improve performance.

In accordance with an embodiment, the health maintenance system 100 may have utility in gaming field. For example, the trained first robotic system 104a may be utilized along with a gaming apparatus (not shown) for controlling a difficulty level of a game. In such a scenario, when a player is playing the game, the local AI-based system 124, under the control of the main AI-based system 114, may determine the external and internal responses exhibited by the player and change the difficulty level of the game based on the external and internal responses. Beneficially, this increases the engagement of the player with the game as per his own specific unique characteristics.

In accordance with an embodiment, the main AI-based system 114 and/or the local AI-based system 124 may be configured generate a targeted physical therapy plan for the target user 130. The targeted physical therapy plan may be generated based on the combination of the first set of responses, the second set of responses, the current health state, and the target health state. The main AI-based system 114 and/or the local AI-based system 124 may be further configured to monitor various responses exhibited by the target user 130 during the course of the targeted physical therapy plan for keeping a track of the changing physical ability of the target user 130. The main AI-based system 114 and/or the local AI-based system 124 may be further configured to adjust the targeted physical therapy plan based on the changes observed in the physical ability of the target user 130.

FIG. 2 illustrates different components of a server arrangement and a robotic system of the health maintenance system of FIG. 1, in accordance with an exemplary embodiment of the disclosure. FIG. 2 is described in conjunction with elements from FIG. 1. With reference to FIG. 2, there is shown the server arrangement 102 and the first robotic system 104a of the health maintenance system 100 of FIG. 1. The server arrangement 102 may further include a control circuitry 202, a main storage system 204, and a network interface 206. The main storage system 204 may store a medical knowledge database 208 and the OSMR dataset. Hereinafter, the OSMR dataset stored in the main storage system 204 is designated and referred to as "the OSMR dataset 210". The main AI-based system 114 may include a neural network schema 212.

The first robotic system 104a may further include a local storage system 214, a display 216, and a network interface 218. The local storage system 214 may store a medical knowledge database 220 and the OSMR dataset. Hereinafter, the OSMR dataset stored in the local storage system 214 is designated and referred to as "the OSMR dataset 222". The display 216 may be associated with one or more UIs, such as a UI 216a. The first robotic system 104a may further include the plurality of different stimulus sub-devices 106 that may be detachably attached to the stimulus device 118 by way of a plurality of slots 224 included in the stimulus device 118. The plurality of different stimulus sub-devices 106 may include an odor emitter sub-device 106a, a vibrator sub-device 106b, a pressure sub-device 106c, an integrated digital therapeutic environment (IDTE) generator sub-device 106d, a magnetic field generator sub-device 106e, a touch-sense sub-device 106f, a temperature sub-device 106g, a VR scene projecting sub-device 106h, and a sound wave control sub-device 106i. A person of ordinary skill in the art will understand that the server arrangement 102 and the first robotic system 104a may also include other suitable components or systems, in addition to the components or systems which are illustrated herein to describe and explain the function and operation of the present disclosure.

The control circuitry 202 may comprise suitable logic, circuitry, and/or interfaces configured to execute a set of instructions stored in the main storage system 204. The control circuitry 202 may be configured to implement the training phase and the operational phase (as described in FIG. 1) for providing targeted physical therapy to various target users, for example the target user 130. The control circuitry 202 may be configured to generate the OSMR dataset 210 in the training phase (as described in FIG. 1). The control circuitry 202 may be configured to convert the primary information and the supplementary information into the AI-based system-readable data format. Examples of the control circuitry 202 may be an X86-based processor, a RISC processor, an ASIC processor, a CISC processor, a microcontroller, a CPU, a GPU, a state machine, and/or other processors or circuits.

The main storage system 204 may comprise suitable logic, circuitry, and/or interfaces configured to store a machine code and/or a set of instructions with at least one code section executable by the control circuitry 202. The main storage system 204 may store the medical knowledge database 208 and the OSMR dataset 210. The medical knowledge database 208 may include details pertaining to available medical literature. For example, the medical knowledge database 208 may include medical e-books, research papers, and/or medical case studies. The main storage system 204 may store one or more machine learning algorithms (for example, deep learning algorithms or other types of artificial intelligence algorithms) that enable the main AI-based system 114 to implement the training phase based on the medical knowledge database 208 and the OSMR dataset 210. Examples of implementation of the main storage system 204 may include, but are not limited to, an Electrically Erasable Programmable Read-Only Memory (EEPROM), a Random Access Memory (RAM), a Read Only Memory (ROM), a Hard Disk Drive (HDD), a Flash memory, a Secure Digital (SD) card, a Solid-State Drive (SSD), and/or a CPU cache memory.

The network interface 206 may comprise suitable logic, circuitry, interfaces, and/or code that may be configured to connect and communicate with a plurality of devices in the network environment of the health maintenance system 100. The network interface 206 may implement known technologies to support wireless communication. The network interface 206 may include, but are not limited to an antenna, a radio frequency (RF) transceiver, one or more amplifiers, a tuner, one or more oscillators, a digital signal processor, a coder-decoder (CODEC) chipset, a subscriber identity module (SIM) card, and/or a local buffer. The network interface 206 may communicate via offline and online wireless communication with networks, such as the Internet, an Intranet, and/or a wireless network, such as a cellular telephone network, a wireless local area network (WLAN), personal area network, and/or a metropolitan area network (MAN). The wireless communication may use any of a plurality of communication standards, protocols and technologies, such as Global System for Mobile Communications (GSM), Enhanced Data GSM Environment (EDGE), wideband code division multiple access (W-CDMA), code division multiple access (CDMA), LTE 4G, 5G, time division multiple access (TDMA), Bluetooth, Wireless Fidelity (Wi-Fi) (such as IEEE 802.11, IEEE 802.11b, IEEE 802.11g, IEEE 802.11n, and/or any other IEEE 802.11 protocol), voice over Internet Protocol (VoIP), Wi-MAX, Internet-of-Things (IoT) technology, Machine-Type-Communication (MTC) technology, a protocol for email, instant messaging, and/or Short Message Service (SMS).

The neural network schema 212 may refer to a neural network architecture having a number of layers, such as an input layer, an output layer, and intermediate layers that operates on data received at the input layer to generate corresponding output at the output layer. The neural network schema 212 may also be referred to as a neural network model. The neural network schema 212 of the main AI-based system 114 may be provided with unlabeled, uncategorized data of the stimulus-response pairs in the AI-based system-readable data format and the main AI-based system 114 may act on the data to automatically find structure and pattern in the stimulus-response pairs by extracting features and analyzing its pattern to draw inferences.

The local storage system 214 includes suitable logic, circuitry, and/or interfaces that may be configured to store a machine code and/or a set of instructions with at least one code section executable by the control circuitry 116. The local storage system 214 may store a medical knowledge database 220 and an OSMR dataset 222. The medical knowledge database 220 may be similar to the medical knowledge database 208 and may include details pertaining to the available medical literature. The OSMR dataset 222 is a local instance of the OSMR dataset 210. The local storage system 214 may store one or more machine learning algorithms (for example, deep learning algorithms or other types of artificial intelligence algorithms) that enable the local AI-based system 124 to execute one or more corresponding operations during the offline mode and the online mode. Examples of implementation of the local storage system 214 may include, but are not limited to, an EEPROM, a RAM, a ROM, an HDD, a Flash memory, an SD card, an SSD, and/or a CPU cache memory.

The display 216 may comprise suitable logic, circuitry, and/or interfaces configured to receive the user information of the target user 130, who is in need of physical therapy. In accordance with an embodiment, the display 216 may be a touch screen display that may receive an input from the target user 130 or the operator of the first robotic system 104a. Examples of the display 216 may include, but are not limited to, a see-through display, a projection-based display, a smart-glass display, and/or an electro-chromic display. The display 216 may be a transparent or a semi-transparent display screen. The user interface 216a may be rendered at the display 216 under the control of the control circuitry 116.

The network interface 218 may comprise suitable logic, circuitry, interfaces, and/or code that may be configured to connect and communicate with a plurality of devices in the network environment of the health maintenance system 100. The network interface 218 may be similar to that of the network interface 206.

The plurality of slots 224 may correspond to attachment means for the stimulus device 118 for attaching one or more of the plurality of different stimulus sub-devices 106 as and when required. For example, in a modular arrangement, the odor emitter sub-device 106a, the vibrator sub-device 106b, the pressure sub-device 106c, the IDTE generator sub-device 106d, the magnetic field generator sub-device 106e, the touch-sense sub-device 106f, the temperature sub-device 106g, the VR scene projecting sub-device 106h, and the sound wave control sub-device 106i may be detachably attached to the stimulus device 118 by using the plurality of slots 224.

The odor emitter sub-device 106a may comprise suitable logic, circuitry, and/or interfaces configured to emit different types of odor as output. For example, the odor emitter sub-device 106a may be configured to spray liquid or gas for emitting the different types of odor. The intensity of the output may be controlled based on an amount of the liquid or gas sprayed. The odor emitted by the odor emitter sub-device 106a may stimulate smelling sense of a user.

The vibrator sub-device 106b may comprise suitable logic, circuitry, and/or interfaces configured to generate vibrations as output. The intensity of the output may be controlled by controlling the intensity of generated vibrations. The vibrations generated by the vibrator sub-device 106b may stimulate touch sense of a user. The pressure sub-device 106c may comprise suitable logic, circuitry, and/or interfaces configured to provide calibrated pressure as output. The intensity of the output may be controlled by controlling the intensity of the pressure. The pressure provided by the pressure sub-device 106c may stimulate the touch sense of a user.

The IDTE generator sub-device 106d may comprise suitable logic, circuitry, interfaces, and/or code that may be configured to output a customized digital therapeutic environment around a user as output. The digital therapeutic environment generator 106d may control the customized digital therapeutic environment by use of various modules and devices, of the health maintenance system 100. Examples of implementations of the digital therapeutic environment generator 106d may be an X86-based processor, a GPU, a RISC processor, an ASIC processor, a CISC processor, a microcontroller, a CPU, a specialized hardware generator, and/or other control circuits.

The magnetic field generator sub-device 106e may comprise suitable logic, circuitry, and/or interfaces configured to generate magnetic field around a user as output. The touch-sense sub-device 106f may comprise suitable logic, circuitry, and/or interfaces configured to stimulate touch sense of a user.

The temperature sub-device 106g may comprise suitable logic, circuitry, and/or interfaces configured to provide hot and cold application to a user. In one example, the temperature sub-device 106g may include IR lamps for providing hot application to the user.

The VR scene projecting sub-device 106h may comprise suitable logic, circuitry, and/or interfaces configured to project audio-visual scenes around a user for physical therapy. The audio-visual scenes projected by the VR scene projecting sub-device 106h may stimulate hearing and visual senses of the user. Examples of implementations of the VR scene projecting sub-device 106h may be an X86-based processor, a GPU, a RISC processor, an ASIC processor, a CISC processor, a microcontroller, a CPU, a specialized hardware generator, and/or other control circuits.

The sound wave control sub-device 106i may comprise suitable logic, circuitry, and/or interfaces configured to generate sound waves as output. The sound waves generated by the sound wave control sub-device 106i may stimulate hearing sense of a user. It will be apparent to those of skill in the art that the plurality of different stimulus sub-devices 106 may include other sub-devices as well, for example, an exercise mechanism that enables planned movement in various body portions (for example, arms, wrists, legs, thighs, neck, feet, and/or back) of the user for exercising.

Figure 3A:
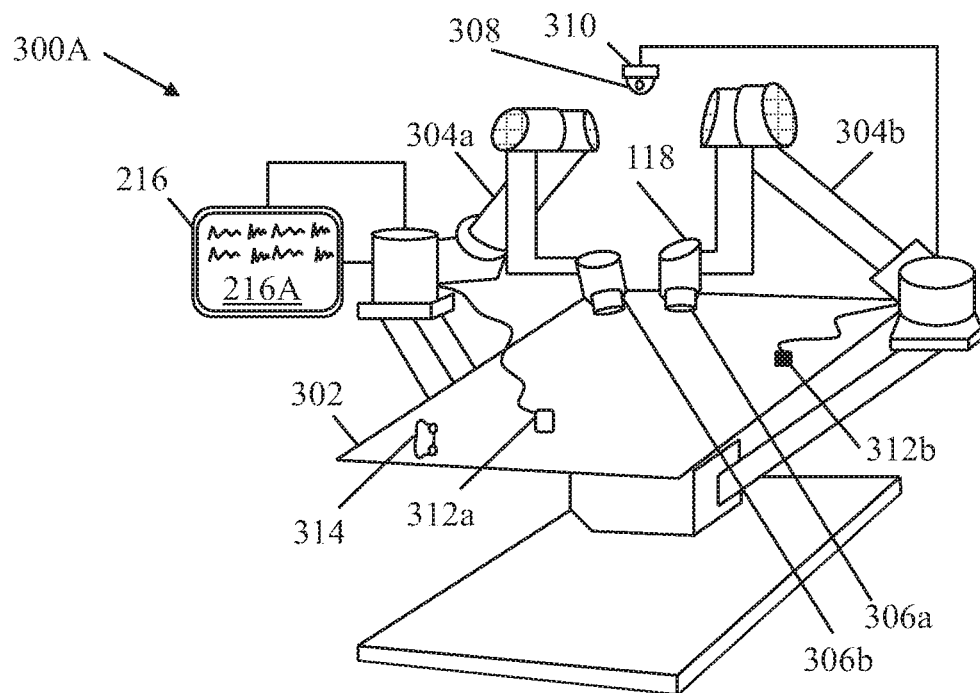
FIG. 3A illustrates an exemplary robotic system, in accordance with an embodiment of the disclosure.

FIG. 3A illustrates an exemplary robotic system, in accordance with an embodiment of the disclosure. FIG. 3A is described in conjunction with elements from FIGS. 1 to 2. With reference to FIG. 3A, there is shown a robotic system 300A for providing physical therapy to users. The robotic system 300A may correspond to the first robotic system 104a (of FIG. 1).

The robotic system 300A is shown to include a table structure 302 for the target user 130 to lie down, and two arms 304a and 304b. The two arms 304a and 304b are equipped with two stimulus sub-devices 306a and 306b included in the plurality of different stimulus sub-devices 106. The robotic system 300A further includes the display 216 that has the UI 216a rendered thereon. The UI 216a may be used to receive an input from a user (e.g. the target user 130 or a health care operator). This may be to initiate the provisioning of a physical therapy, to change a setting of the robotic system 300A, or to test run the robotic system 300A. The robotic system 300A is communicatively coupled to (by wired or wireless medium) a 360-degree projector (hereinafter, referred to as a "projector 308") for creating a digital therapeutic environment. The robotic system 300A further includes an imaging device 310 (i.e., an external response sensor) that may be configured to obtain one or more images of the target user 130 when the target user 130 undergoes physical therapy by using the robotic system 300A. The one or more images are indicative of the facial expressions and the gestures of the target user 130. The robotic system 300A further includes, for example, two internal response sensors 312a and 312b that may be attached to a body of the target user 130 in a non-invasive manner when the target user 130 undergoes physical therapy by using the robotic system 300A. The robotic system 300A further includes a VR headset 314 that creates VR scenes for the target user 130. For the sake of brevity, other components (as described in FIG. 2) of the robotic system 300A are not shown in FIG. 3A.

Figure 3B:
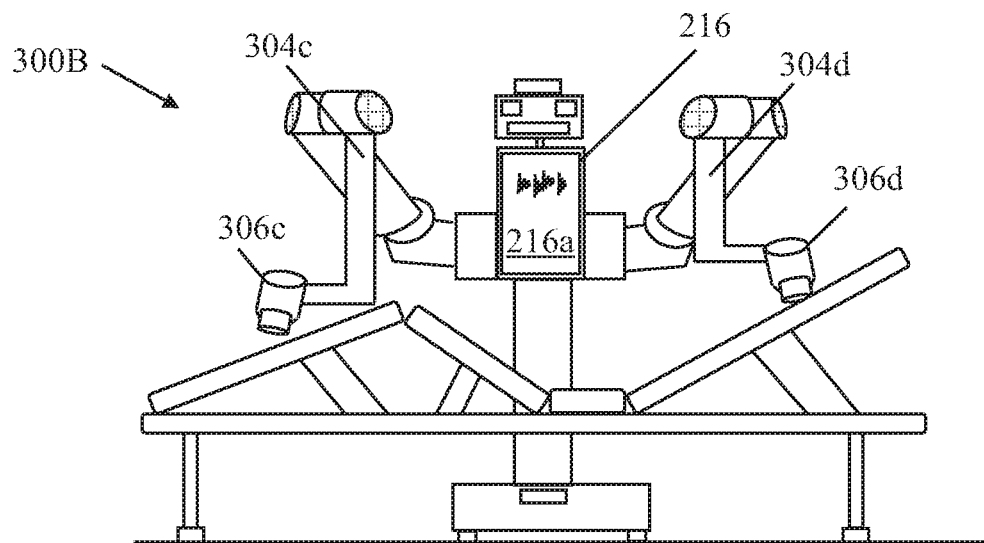
FIG. 3B illustrates an exemplary robotic system, in accordance with another embodiment of the disclosure.

FIG. 3B illustrates an exemplary robotic system, in accordance with another embodiment of the disclosure. FIG. 3B is described in conjunction with elements from FIGS. 1 to 2. With reference to FIG. 3B, there is shown another robotic system 300B for providing physical therapy to users. The robotic system 300B may correspond to the first robotic system 104a (of FIG. 1). The robotic system 300B is shown to be a robot that has two arms 304c and 304d each equipped with a corresponding stimulus sub-device 306c and 306d. The robotic system 300B further includes the display 216 that has the UI 216a rendered thereon. It will be apparent to a person of ordinary skill in the art that the robotic system 300B of FIG. 3B further includes other components that are described in FIG. 2.

Figure 3C:
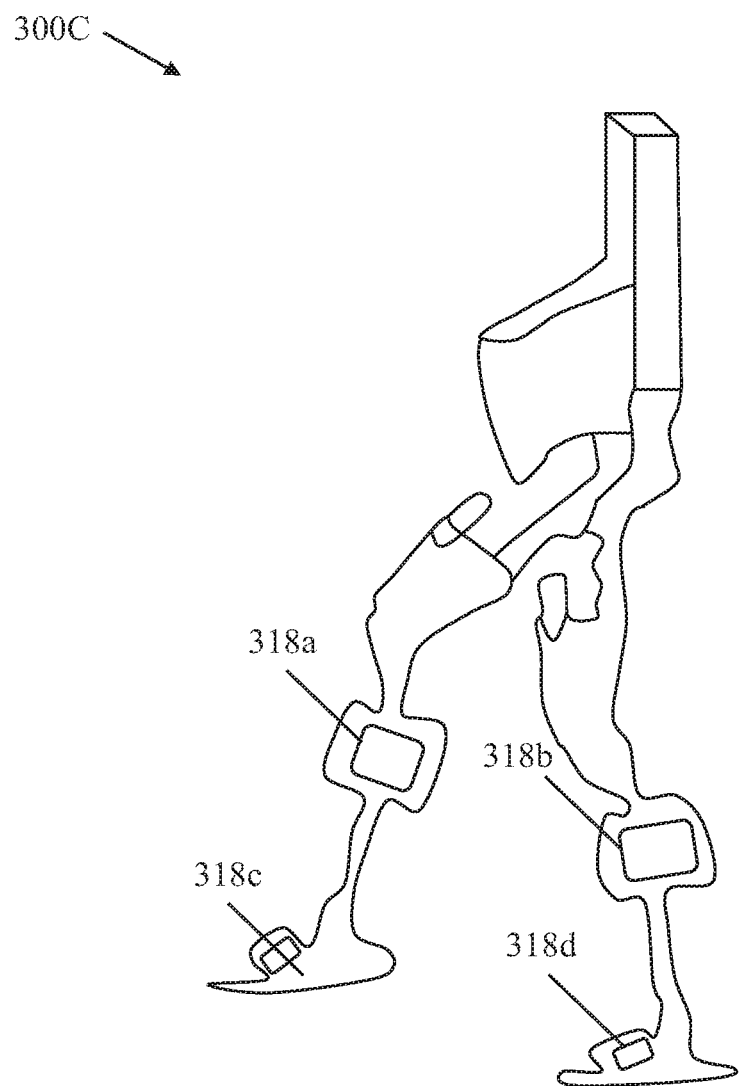
FIG. 3C illustrates an exemplary robotic system, in accordance with yet another embodiment of the disclosure.

FIG. 3C illustrates an exemplary robotic system, in accordance with yet another embodiment of the disclosure. FIG. 3C is described in conjunction with elements from FIGS. 1 to 2. With reference to FIG. 3C, there is shown another robotic system 300C for providing physical therapy to users. The robotic system 300C may correspond to the first robotic system 104a (of FIG. 1). The robotic system 300C is shown to be an exoskeleton device that may be worn by the target user 130 who wants physical therapy. The robotic system 300C includes, for example, four internal response sensors 318a-318d that may come in contact with the body of the target user 130, when the target user 130 wears the robotic system 300C for physical therapy. It will be apparent to a person of ordinary skill in the art that the robotic system 300C of FIG. 3C includes all other components that are described in FIG. 2.

Figure 4A:
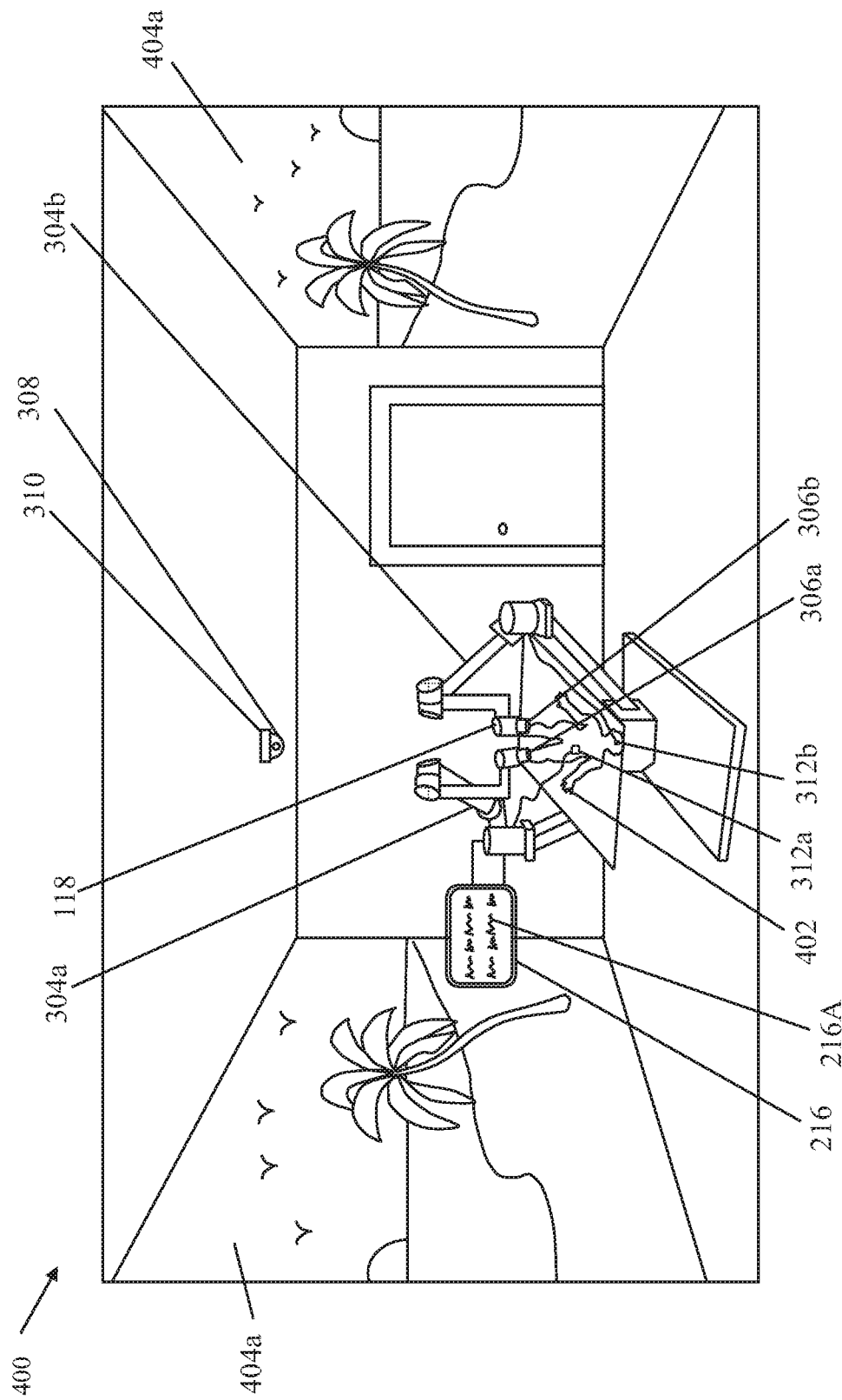
FIGS. 4A and 4B collectively, illustrate an exemplary scenario for implementation of the health maintenance system of FIG. 1 with robotic system, in accordance with an exemplary embodiment of the disclosure.
Figure 4B:
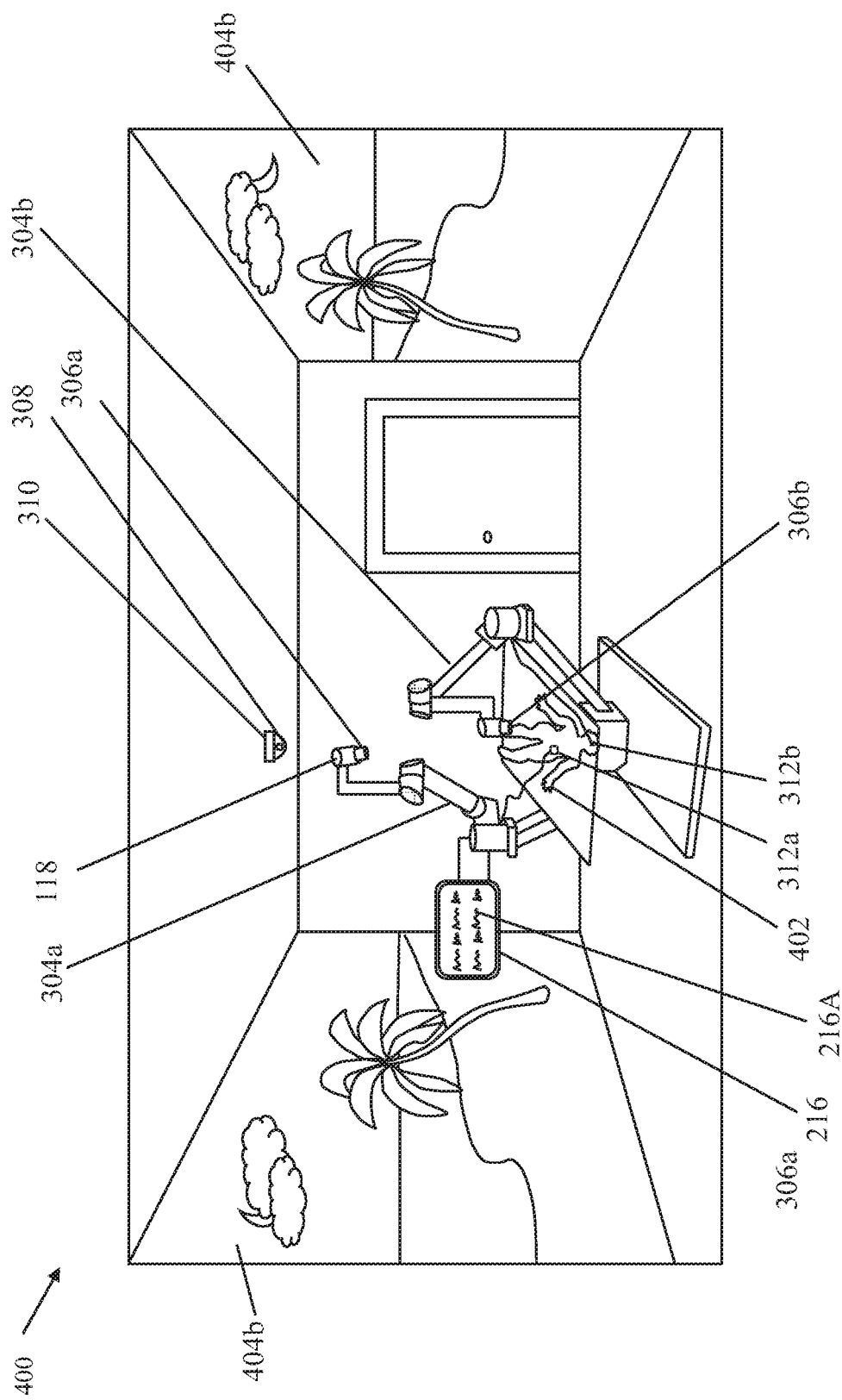

FIGS. 4A and 4B collectively, illustrate an exemplary scenario for implementation of the health maintenance system with robotic system, in accordance with an exemplary embodiment of the disclosure. FIGS. 4A and 4B are described in conjunction with elements from FIGS. 1, 2, and 3A. With reference to FIGS. 4A and 4B, there is shown an exemplary scenario 400 that depicts the robotic system 300A configured to provide physical therapy to a subject 402. In an example, the subject 402 may be a sportsman, a student, a patient, or any person who intend to improve his current health state. The robotic system 300A and the subject 402 may correspond to the first robotic system 104a and the target user 130, respectively of FIG. 1. The robotic system 300A may be communicatively coupled with the server arrangement 102.

With reference to FIG. 4A, the subject 402 may be unable to move lower limbs (i.e., the current health state) and may utilize the robotic system 300A for undergoing physical therapy to initiate movement in the lower limbs (i.e., the target health state). The UI 216a may be utilized by the subject 402 or a health care operator for providing the user information of the subject, for example, details pertaining to the current health state, the target health state, and the supplementary information of the subject 402. In one embodiment, if the subject 402 had undergone physical therapy previously, the subject 402 may also provide details pertaining to a stimulus that was used in the previous physical therapy session. For the sake of brevity, it is assumed that the robotic system 300A is operating in the offline mode.

Based on the current health state, the target health state, and the supplementary information of the subject 402, the trained local AI-based system 124 may retrieve the priori stimulus and determine the set of test stimuli for the subject 402. The determined set of test stimuli may include applying vibration input, having intensity at a first level, in a circular manner on both lower limbs of the subject 402 for the first test duration, for example, five minutes. The determined set of test stimuli may further include presenting a VR-based therapeutic environment to the subject 402.

The control circuitry 116 may then control the stimulus device 118 for applying the set of test stimuli to the body of the subject 402. The stimulus device 118 may utilize the stimulus sub-devices 306a and 306b for applying the vibration input, having intensity at the first level, in a circular manner on both lower limbs of the subject 402. The stimulus device 118 may provide the vibration input on both lower limbs of the subject 402 for the first test duration. The projector 308, under the control of the control circuitry 116, may create a view 404a in a physical enclosure, such as room, depicting sunset at a beach for presenting the VR-based therapeutic environment to the subject 402. The two internal response sensors 312a and 312b are shown to be attached to the body of the subject 402 in a non-invasive manner and the imaging device 310 is turned-on for obtaining the one or more images of the subject 402 while the subject 402 undergoes physical therapy. Due to the application of the vibration input, the first set of responses may be generated in the body of the subject 402 and the second set of responses may be discernible from the external surface of the body of the subject 402. For example, the two internal response sensors 312a and 312b may sense that muscle tension in the lower left limb of the subject 402 is higher as compared to muscle tension in the lower right limb of the subject 402. The two internal response sensors 312a and 312b may further sense that the subject 402 is experiencing pain the lower left limb due to the application of the vibration input, based on the identified activity in the brain area that is associated with pain. The imaging device 310 obtains the one or more images for sensing the facial expressions of the subject 402 while the subject 402 is undergoing physical therapy. The change in the facial expressions of the subject 402, for example, frown lines on forehead, may indicate that the subject 402 is not in a relaxed state.

The local AI-based system 124 may then process sensor data obtained by the two internal response sensors 312a and 312b and the imaging device 310. The sensor data may indicate the first set of responses and the second set of responses exhibited by the subject 402. Based on the processing of the sensor data, the local AI-based system 124 may determine that the subject 402 is experiencing pain in their lower left limb due to the application of the vibration input. Thus, the local AI-based system 124 may determine a new stimulus having a new set of stimulus parameters based on the combination of the first set of responses, the second set of responses, the current health state and the target health state. The new stimulus may include applying a vibration input, having intensity at a second level, only to the lower right limb of the subject 402 in a random manner for the second duration, for example half hour. The new stimulus may further include presenting another view depicting a visualization of night time at the beach area.

With reference to FIG. 4B, the control circuitry 116 may calibrate the set of stimulus parameters of the stimulus device 118 for providing the new stimulus to the subject 402. In one example, under the control of the control circuitry 116, the stimulus device 118 discontinues to apply the vibration input to the lower left limb of the subject 402 and the stimulus device 118 utilizes the second sub-stimulus device 306b for applying the vibration input, having intensity at the second level, to the lower right limb of the subject 402 in a random manner for the second duration. Further, the projector 308, under the control of the control circuitry 116, may create another view 404b for depicting a visualization of night time at the beach area. Due to the repeated application of the new stimulus to the subject 402, the physical ability of the subject 402 may improve and movement may start in the lower limbs of the subject 402. The local AI-based system 124 and the main AI-based system 114 may continuously learn and improve itself based on the identification and measuring the responses to provided stimulus, and accordingly the physical therapy plan may be updated or changed.

Figure 5A:
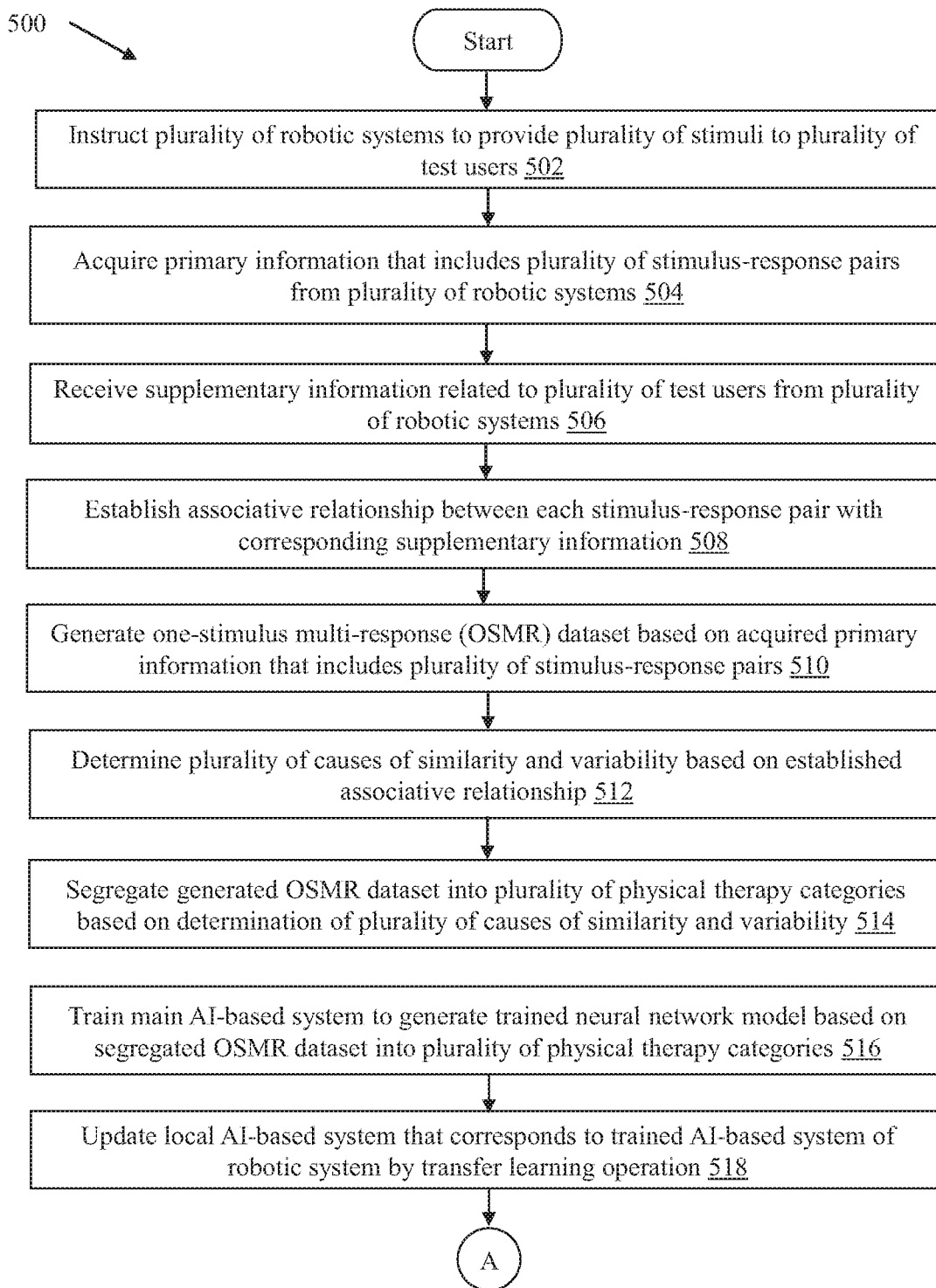
FIGS. 5A, 5B, and 5C collectively, illustrate a method for operation of the robotic system for provisioning physical therapy, in accordance with an exemplary embodiment of the disclosure.
Figure 5B:
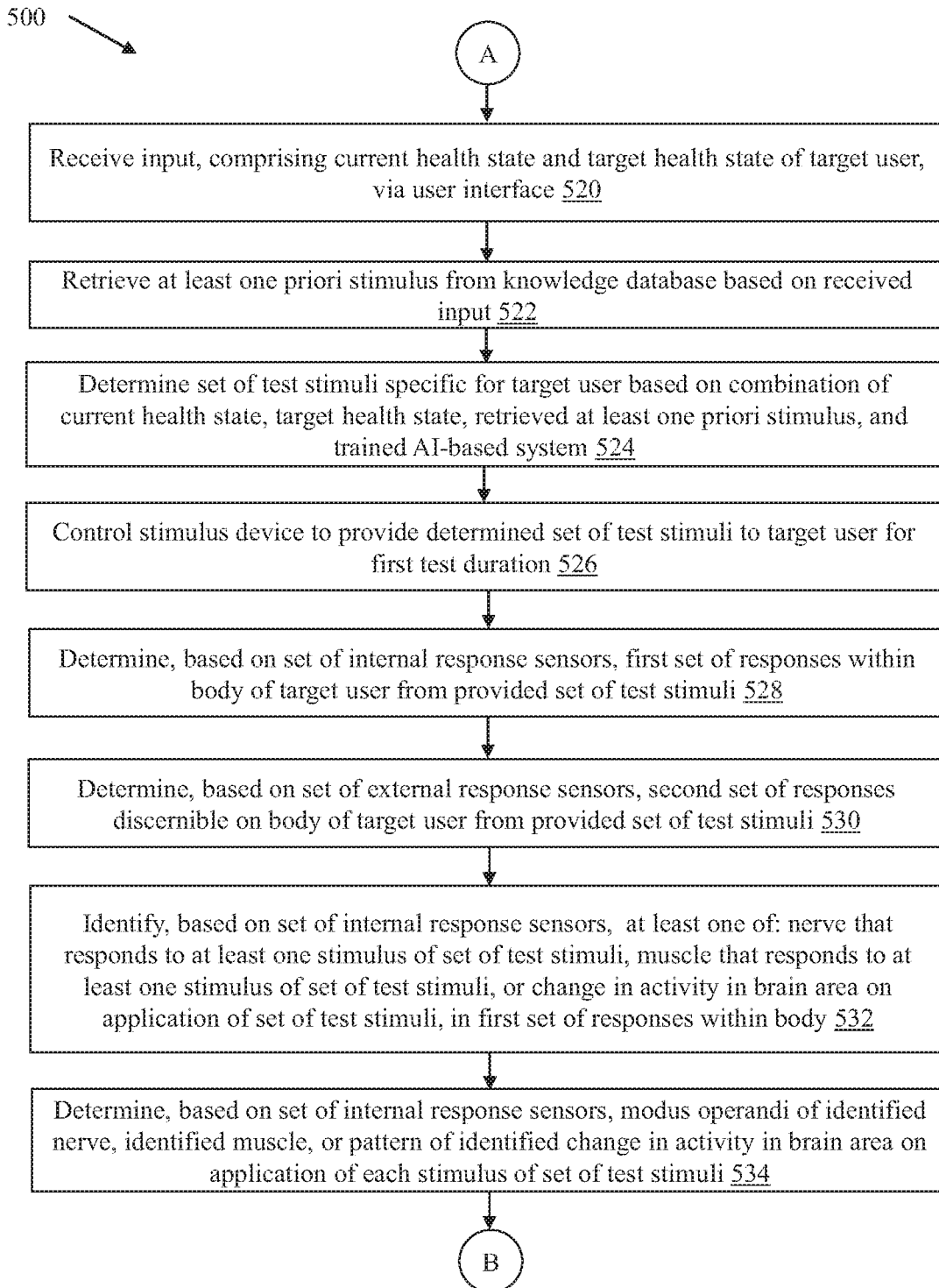
Figure 5C:
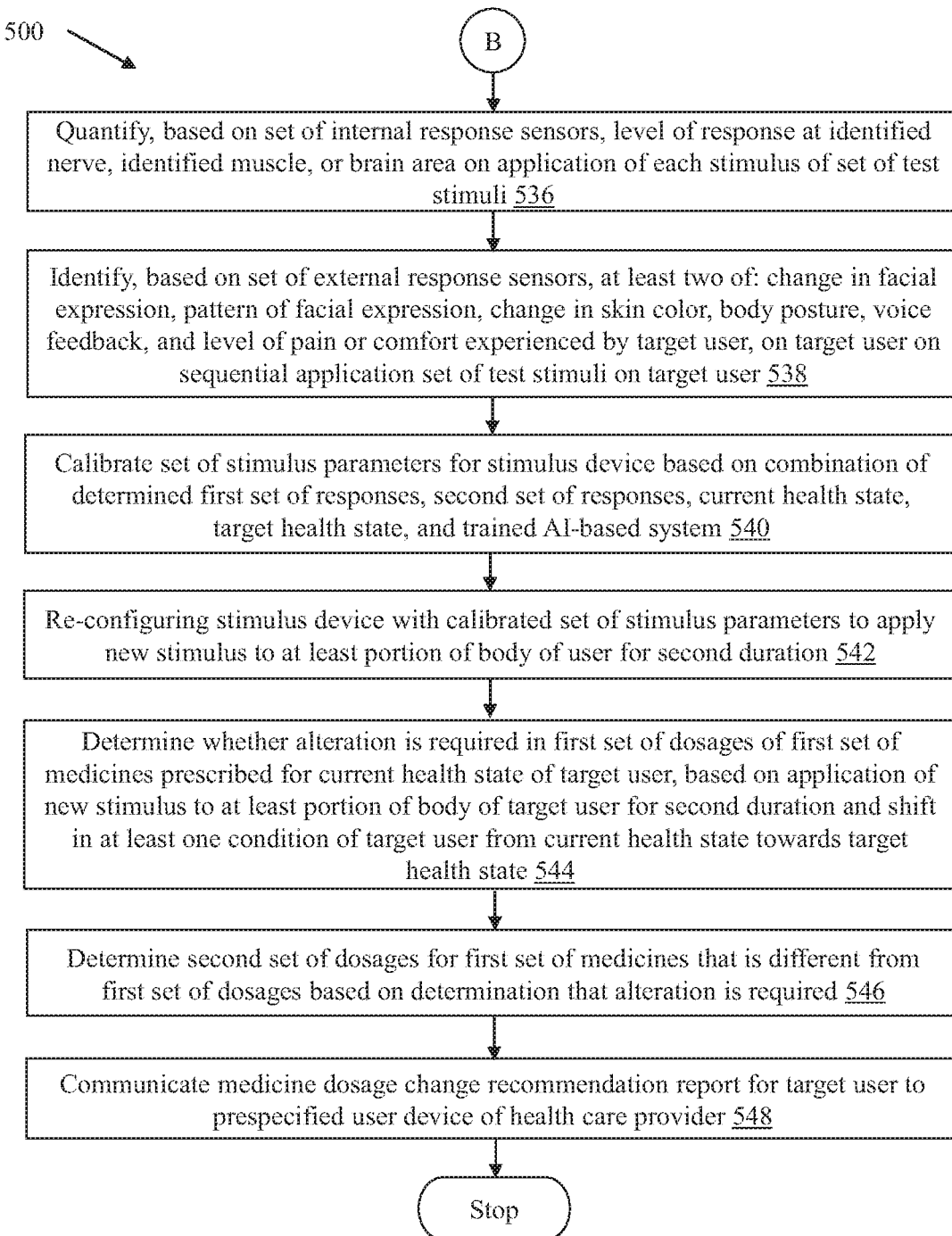

FIGS. 5A, 5B, and 5C collectively, illustrate a method for operation of the robotic system for provisioning physical therapy, in accordance with an exemplary embodiment of the disclosure. FIGS. 5A to 5C are described in conjunction with elements from FIGS. 1, 2, 3A to 3C, 4A, and 4B. With reference to FIGS. 5A to 5C, there is shown a flowchart 500 comprising exemplary operations 502 through 546 by the health maintenance system 100.

At 502, the plurality of robotic systems 104 may be instructed to provide the plurality of stimuli to the plurality of test users 128. The control circuitry 202 may be configured to instruct the plurality of robotic systems 104 to provide the plurality of stimuli to the plurality of test users 128. At 504, the primary information that includes the plurality of stimulus-response pairs may be acquired from the plurality of robotic systems 104. The control circuitry 202 may be configured to acquire the primary information that includes the plurality of stimulus-response pairs from the plurality of robotic systems 104.

At 506, the supplementary information related to the plurality of test users 128 may be received from the plurality of robotic systems 104. The control circuitry 202 may be further configured to receive the supplementary information related to the plurality of test users 128 from the plurality of robotic systems 104. The supplementary information of each test user 128a-128n may include the details pertaining to physical characteristics, a feedback from a physical therapy expert, an age group, a geography, diagnostic information from at least one medical diagnosis test, a medical history, dosages of medicines prescribed for a current health state, and/or the like of the corresponding test user 128a-128n.

At 508, the associative relationship may be established between each stimulus-response pair with corresponding supplementary information. The control circuitry 202 may be configured to establish the associative relationship between each stimulus-response pair with corresponding supplementary information. At 510, the OSMR dataset 210 may be generated based on the acquired primary information that includes the plurality of stimulus-response pairs. The control circuitry 202 may be configured to generate the OSMR dataset 210 based on the acquired primary information that includes the plurality of stimulus-response pairs.

At 512, the plurality of causes of similarity and variability is determined based on the established associative relationship. The main AI-based system 114 may be configured to determine the plurality of causes of similarity and variability based on the established associative relationship. Examples of the plurality of causes of similarity and variability determined by the main AI-based system 114 may include, but are not limited to, age groups, medicine intake, genomic, body weight, BMI, ailment, or the like. At 514, the generated OSMR dataset 210 is segregated into the plurality of physical therapy categories based on the determination of the plurality of causes of similarity and variability. The main AI-based system 114 may be configured to segregate the generated OSMR dataset 210 into the plurality of physical therapy categories, for example, the first physical therapy category, the second physical therapy category, and the third physical therapy category. The first physical therapy category may include the first set of stimulus-response pairs suitable for the group therapy. The second physical therapy category may include the second set of stimulus-response pairs suitable for users having at least one specific trait. The third physical therapy category may include the third set of stimulus-response pairs suitable for a specific user.

At 516, the main AI-based system 114 may be trained to generate the trained neural network model based on the segregated OSMR dataset 210 into the plurality of physical therapy categories. At 518, the local AI-based system 124 that corresponds to the trained local AI-based system 124 of the first robotic system 104a may be updated by transfer learning operation. The main AI-based system 114 may be configured to update the local AI-based system 124 by the transfer learning operation. At 520, an input, comprising the current health state and the target health state of the target user 130 is received, via the UI 216a. The control circuitry 116 may be configured to receive the input, comprising the current health state and the target health state of the target user 130. The control circuitry 116 may be further configured to receive the supplementary information of the target user 130 via the UI 216a.

At 522, at least one priori stimulus may be retrieved from the medical knowledge database 220 based on the received input. The control circuitry 116 may be configured to retrieve the at least one priori stimulus from the medical knowledge database 220. At 524, the set of test stimuli specific for the target user 130 may be determined based on the combination of the current health state, the target health state, the retrieved at least one priori stimulus, and the trained local AI-based system 124. The control circuitry 116 may be configured to utilize the trained local AI-based system 124 for determining the set of test stimuli specific for the target user 130.

At 526, the stimulus device 118 may be controlled to provide the determined set of test stimuli to the target user 130 for the first test duration. The control circuitry 116 may be configured to control the stimulus device 118 for providing the determined set of test stimuli to the target user 130 for the first test duration. The stimulus device 118 may further utilize one or more of the plurality of different stimulus sub-devices 106 for providing the determined set of test stimuli to the target user 130. The one or more of the plurality of different stimulus sub-devices 106 may be detachably attached to the stimulus device 118 in a modular arrangement by way of the plurality of slots 224 in the stimulus device 118.

At 528, the first set of responses within the body of the target user 130 from the provided set of test stimuli may be determined based on the set of internal response sensors 120. The control circuitry 116 may be configured to control the set of internal response sensors 120 for determining the first set of responses generated within the body of the target user 130 due to the application of the set of test stimuli. The set of internal response sensors 120 may be configured to sense and measure the first set of responses generated within the body of the target user 130. At 530, the second set of responses discernible on the body of the target user 130 from the provided set of test stimuli may be determined based on the set of external response sensors 122. The control circuitry 116 may be configured to control the set of external response sensors 122 for determining the second set of responses exhibited by the body of the target user 130 due to the application of the set of test stimuli. The set of external response sensors 122 may be configured to sense and measure the second set of responses exhibited by the body of the target user 130.

At 532, at least one of: a nerve that responds to at least one stimulus of the set of test stimuli, a muscle that responds to at least one stimulus of the set of test stimuli, or a change in the activity in the brain area on the application of the set of test stimuli, in the first set of responses may be identified based on the set of internal response sensors 120. In the first set of responses, the control circuitry 116 may be configured to identify at least one of: the nerve that responds to the at least one stimulus of the set of test stimuli, the muscle that responds to the at least one stimulus of the set of test stimuli, or the change in the activity in the brain area on the application of the set of test stimuli.

At 534, the modus operandi of the identified nerve, the identified muscle, or the pattern of the identified change in the activity in the brain area on the application of each stimulus of the set of test stimuli may be determined. The control circuitry 116 may be configured to determine the modus operandi of the identified nerve, the identified muscle, or the pattern of the identified change in the activity in the brain area on the application of each stimulus of the set of test stimuli. At 536, the level of the response at the identified nerve, the identified muscle, or the brain area on the application of each stimulus of the set of test stimuli may be quantified based on the set of internal response sensors 120. The control circuitry 116 may be configured to quantify the level of the response at the identified nerve, the identified muscle, or the brain area on the application of each stimulus of the set of test stimuli.

At 538, based on the set of external response sensors 122, at least two of: the change in facial expression, the pattern of facial expression, the change in skin color, the body posture, the voice feedback, and the level of pain or comfort experienced, on the target user 130 on the sequential application the set of test stimuli on the target user 130, may be identified. The control circuitry 116 may be configured to utilize the set of external response sensors 122 for identifying at least two of: the change in facial expression, the pattern of facial expression, the change in skin color, the body posture, the voice feedback, and the level of pain or comfort experienced, on the target user 130 on the sequential application the set of test stimuli on the target user 130.

At 540, the set of stimulus parameters for the stimulus device 118 may be calibrated based on the combination of the determined first set of responses, the second set of responses, the current health state, the target health state, and the trained local AI-based system 124. The trained local AI-based system 124, under the control of the control circuitry 116, may be configured to calibrate the set of stimulus parameters for the stimulus device 118. At 542, the stimulus device 118 may be re-configured with the calibrated set of stimulus parameters to apply a new stimulus to at least a portion of the body of the target user 130 for a second duration. Thus, the control circuitry 116 may be configured to re-configure the stimulus device 118 with the calibrated set of stimulus parameters to apply the new stimulus to at least the portion of the body of the target user 130 for the second duration. The use of the new stimulus may shift at least one condition of the target user 130 from the current health state towards the target health state. For calibrating the set of stimulus parameters for the stimulus device 118, the control circuitry 116 may be configured to generate the physical stimulation instructions pack specific for the target user 130 based on the second output from the trained local AI-based system 124. The control circuitry 116 may be further configured to activate one or more of the plurality of different stimulus sub-devices 106 at a given timepoint in the second duration in accordance with the generated physical stimulation instructions pack. The physical stimulation instructions pack may include the type of control signal for the plurality of different stimulus sub-devices 106, the time schedule that defines the specific activation time and the specific duration to generate the output in the second duration, the intensity of the output, and the set of sense identifiers.

At 544, whether an alteration is required in the first set of dosages of the first set of medicines prescribed for the current health state of the target user 130 may be determined, based on the application of the new stimulus to the at least portion of the body of the target user 130 for the second duration and the shift in the at least one condition of the target user 130 from the current health state towards the target health state. The control circuitry 116 may be configured to determine whether the alteration is required in the first set of dosages of the first set of medicines prescribed for the current health state of the target user 130. At 546, a second set of dosages for the first set of medicines that is different from the first set of dosages may be determined based on the determination that alteration is required. The control circuitry 116 may be configured to determine the second set of dosages for the first set of medicines. At 548, the medicine dosage change recommendation report for the target user 130 may be communicated to the prespecified user device 126 of the health care provider 108. The network interface 218, under the control of the control circuitry 116, may be configured to communicate the medicine dosage change recommendation report for the target user 130 to the user device 126 of the health care provider 108.

Thus, the health maintenance system 100 including the server arrangement 102 and the plurality of AI-based robotic systems 104 is able to provide physical therapy, which may be used specifically for an individual or for a group therapy. Such physical therapy may result in improving a current health state of a user and achieving a target health state. The health maintenance system 100 provides a technology that has the potential to become an alternative form of treatment for diseases without the need of taking medicines or at least complement and improve the existing model by reducing the usage and dosage of medicines, and thereby avoiding or reducing the side effects of medicines. Technological improvements in the health maintenance system 100 has made the AI-based robotic system 104a to be highly receptive to various responses generated in a body of a user due to the provisioning of physical therapy. Such AI-based robotic system 104a is capable of adjusting the physical therapy as per the responses generated. Further, the AI-based robotic system 104a is able to provide quantifiable feedback on the progress and performance of the user.

Various embodiments of the disclosure may provide a non-transitory computer-readable medium having stored thereon, computer implemented instruction that when executed by a computing device causes a device to execute operations similar to the operations disclosed herein for the operation of the robotic system for physical therapy.

While various embodiments described in the present disclosure have been described above, it should be understood that they have been presented by way of example, and not limitation. It is to be understood that various changes in form and detail can be made therein without departing from the scope of the present disclosure. In addition to using hardware (e.g., within or coupled to a central processing unit ("CPU" or processor), microprocessor, micro controller, digital signal processor, processor core, system on chip ("SOC") or any other device), implementations may also be embodied in software (e.g. computer readable code, program code, and/or instructions disposed in any form, such as source, object or machine language) disposed for example in a non-transitory computer-readable medium configured to store the software. Such software can enable, for example, the function, fabrication, modeling, simulation, description and/or testing of the apparatus and methods describe herein. For example, this can be accomplished through the use of general program languages (e.g., C, C++), hardware description languages (HDL) including Verilog HDL, VHDL, and so on, or other available programs. Such software can be disposed in any known non-transitory computer-readable medium, such as semiconductor, magnetic disc, or optical disc (e.g., CD-ROM, DVD-ROM, etc.). The software can also be disposed as computer data embodied in a non-transitory computer-readable transmission medium (e.g., solid state memory any other non-transitory medium including digital, optical, analogue-based medium, such as removable storage media). Embodiments of the present disclosure may include methods of providing the apparatus described herein by providing software describing the apparatus and subsequently transmitting the software as a computer data signal over a communication network including the internet and intranets.

It is to be further understood that the system described herein may be included in a semiconductor intellectual property core, such as a microprocessor core (e.g., embodied in HDL) and transformed to hardware in the production of integrated circuits.

Additionally, the system described herein may be embodied as a combination of hardware and software. Thus, the present disclosure should not be limited by any of the above-described exemplary embodiments, but should be defined only in accordance with the following claims and their equivalents.

What is claimed is:

1. A robotic system for physical therapy, comprising:
   a stimulus device configured to generate a stimulus;
   a set of external response sensors configured to sense and measure an external response discernible on a body of a user on application of the stimulus;
   a set of internal response sensors configured to sense and measure an internal response within the body of the user on the application of the stimulus from the stimulus device;
   a user interface;
   a server arrangement that comprises a first artificial intelligence (AI)-based system, wherein the server arrangement in a training phase of the first AI-based system, is configured to:
   instruct a plurality of robotic systems that includes the robotic system to apply a plurality of stimuli to a plurality of test users;
   acquire primary information, that includes a plurality of stimulus-response pairs from the plurality of robotic systems, based on a plurality of responses from the set of internal response sensors and the set of external response sensors of each robotic system of the plurality of robotic system, wherein
   the plurality of responses includes the external response and the internal response, and
   each stimulus-response pair of the plurality of stimulus-response pairs is indicative of:
   a type of the stimulus, of the plurality of stimuli, that was applied and a level of a corresponding response that was generated based on the applied stimulus;

generate one-stimulus multi-response (OSMR) dataset based on the acquired primary information that includes the plurality of stimulus-response pairs; and update a second AI-based system based on the OSMR dataset;

control circuitry configured to:

receive an input via the user interface, wherein the input comprises a current health state and a target health state of the user;

retrieve at least one priori stimulus from a knowledge database based on the received input;

determine a set of test stimuli specific for the user based on a combination of the current health state, the target health state, the retrieved at least one priori stimulus, and the updated second AI-based system;

control the stimulus device to apply the determined set of test stimuli to the user for a first test duration;

determine, based on the set of external response sensors, a set of responses discernible on the body of the user from the applied set of test stimuli;

calibrate a set of stimulus parameters for the stimulus device based on a combination of the determined set of responses, the current health state, the target health state, and the updated second AI-based system; and re-configure the stimulus device with the calibrated set of stimulus parameters to apply a new stimulus to at least a portion of the body of the user for a second duration, wherein the use of the new stimulus shifts at least one condition of the user from the current health state towards the target health state; and a phase array antenna component configured to:

generate waves in a specific frequency range to monitor health of one or more organs of the body of the user providing a health monitoring functionality; and function as a fixed wireless access (FWA) for 4G or 5G communication along with the health monitoring functionality, thereby providing dual functionality.

2. The robotic system according to claim 1, wherein the control circuitry is further configured to receive supplementary information via the user interface, the supplementary information includes at least two of physical characteristics of the user, a geography, a feedback from a physical therapy expert, a first set of dosages of a first set of medicines prescribed for the current health state of the user, or diagnostic information from at least one medical diagnosis test, and the received supplementary information is fed to the first AI-based system in addition to the input of the current health state and the target health state.

3. The robotic system according to claim 1, wherein the control circuitry is further configured to identify, based on the set of internal response sensors and the application of the set of test stimuli, at least one of a nerve that responds to at least a first stimulus of the set of test stimuli, a muscle that responds to at least a second stimulus of the set of test stimuli, or a change in an activity in a brain area on the application of the set of test stimuli, in the set of responses within the body.

4. The robotic system according to claim 3, wherein the control circuitry is further configured to determine, based on the set of internal response sensors, a modus operandi of the nerve, the muscle, or a pattern of the change in the activity in the brain area on the application of each stimulus of the set of test stimuli.

5. The robotic system according to claim 3, wherein the control circuitry is further configured to quantify, based on the set of internal response sensors, a level of response at the nerve, the muscle, or the brain area on the application of each stimulus of the set of test stimuli.

6. The robotic system according to claim 1, wherein the control circuitry is further configured to identify, based on the set of external response sensors, at least two of:

a change in a facial expression of the user on the application of at least one stimulus of the set of test stimuli on the user, a pattern of facial expression of the user on a sequential application of the set of test stimuli on the user, a change in skin color, a body posture, a voice feedback from the user, or a level of pain or comfort experienced by the user based on a deviation in a current user behaviour from a baseline behaviour of the user.

7. The robotic system according to claim 1, wherein the server arrangement in the training phase of the first AI-based system, is further configured to:

acquire supplementary information related to the plurality of test users from the plurality of robotic systems;

establish an associative relationship between each stimulus-response pair of the plurality of stimulus-response pairs with corresponding information from the acquired supplementary information based on the first AI-based system; and determine a plurality of causes of similarity and variability based on the established associative relationship.

8. The robotic system according to claim 1, wherein the server arrangement in the training phase of the first AI-based system, is further configured to:

segregate the generated OSMR dataset into a plurality of physical therapy categories based on a plurality of causes of similarity and variability in the plurality of responses;

train the first AI-based system to generate a trained neural network model based on the segregated OSMR dataset into the plurality of physical therapy categories; and update the second AI-based system of the robotic system by a transfer learning operation from the trained neural network model of the server arrangement to the second AI-based system of the robotic system.

9. The robotic system according to claim 8, wherein the plurality of physical therapy categories includes:

a first physical therapy category that includes a first set of stimulus-response pairs, of the plurality of stimulus-response pairs, suitable for a group therapy;

a second physical therapy category that includes a second set of stimulus-response pairs, of the plurality of stimulus-response pairs, suitable for users having least one specific trait; and a third physical therapy category that includes a third set of stimulus-response pairs, of the plurality of stimulus-response pairs, suitable for a specific user.

10. A method of operation of a robotic system for physical therapy, the method comprising:

instructing, by a server arrangement in a training phase of a first artificial intelligence (AI)-based system, a plurality of robotic systems to apply a plurality of stimuli to a plurality of test users, wherein the server arrangement comprises the first AI-based system;

acquiring, by the server arrangement, primary information that includes a plurality of stimulus-response pairs from the plurality of robotic systems, wherein the acquiring of the primary information is based on a plurality of responses from a set of internal response sensors and a set of external response sensors of each robotic system of the plurality of robotic system, wherein
 each stimulus-response pair of the plurality of stimulus-response pairs is indicative of:
  a type of a stimulus, of the plurality of stimuli, that was applied and
  a level of a corresponding response that was generated based on the applied stimulus;
generating by the server arrangement, one-stimulus multi-response (OSMR) dataset based on the acquired primary information that includes the plurality of stimulus-response pairs; and
updating, by the server arrangement, a second AI-based system of the robotic system based on the OSMR dataset;
receiving, by control circuitry of the robotic system from the plurality of robotic systems, an input via a user interface, wherein the input comprises a current health state and a target health state of a user;
retrieving, by the control circuitry, at least one priori stimulus from a knowledge database based on the received input;
determining, by the control circuitry, a set of test stimuli specific for the user based on a combination of the current health state, the target health state, the retrieved at least one priori stimulus, and the updated second AI-based system of the robotic system;
controlling, by the control circuitry, a stimulus device of the robotic system to apply the determined set of test stimuli to the user for a first test duration;
determining, by the control circuitry, a set of responses discernible on a body of the user from the applied set of test stimuli, wherein the determining of the set of responses discernible on the body of the user is based on the set of external response sensors of the robotic system;
calibrating, by the control circuitry, a set of stimulus parameters for the stimulus device based on a combination of the determined set of responses, the current health state, the target health state, and the updated second AI-based system; and
re-configuring, by the control circuitry, the stimulus device with the calibrated set of stimulus parameters to apply a new stimulus to at least a portion of the body of the user for a second duration, wherein the use of the new stimulus shifts at least one condition of the user from the current health state towards the target health state;
generating, by a phase array antenna component, waves in a specific frequency range to monitor health of one or more organs of the body of the user providing a health monitoring functionality; and
functioning as a fixed wireless access (FWA) for 4G or 5G communication along with the health monitoring functionality, thereby providing dual functionality.

11. The method according to claim 10, further comprising identifying, by the control circuitry, at least one of a nerve that responds to at least a first stimulus of the set of test stimuli, a muscle that responds to at least a second stimulus of the set of test stimuli, or a change in an activity in a brain area on the application of the set of test stimuli, in the first set of responses within the body,
 wherein the identifying is based on the set of internal response sensors and the application of the set of test stimuli.

12. The method according to claim 11, further comprising determining, by the control circuitry, a modus operandi of the nerve, the muscle, or a pattern of the change in the activity in the brain area on the application of each stimulus of the set of test stimuli, based on the set of internal response sensors.

13. The method according to claim 11, further comprising:
 quantifying, by the control circuitry, a level of response at the nerve, the muscle, or the brain area on the application of each stimulus of the set of test stimuli, wherein the quantifying is based on the set of internal response sensors; and
 identifying, by the control circuitry, at least two of:
  a change in a facial expression of the user on the application of at least one stimulus of the set of test stimuli on the user, a pattern of facial expression of the user on a sequential application of the set of test stimuli on the user, a change in skin color, a body posture, a voice feedback from the user, or
  a level of pain or comfort experienced by the user based on a deviation in a current user behavior from a baseline behavior of the user, based on the set of external response sensors.

14. A non-transitory computer readable medium having stored thereon, computer executable instruction, which when executed by a computer, cause the computer to execute operations, the operations comprising:
 instructing, by a server arrangement in a training phase of a first artificial intelligence (AI)-based system, a plurality of robotic systems to apply a plurality of stimuli to a plurality of test users, wherein the server arrangement comprises the first AI-based system;
 acquiring, by the server arrangement, primary information that includes a plurality of stimulus-response pairs from the plurality of robotic systems, wherein the acquiring of the primary information is based on a plurality of responses from a set of internal response sensors and a set of external response sensors of each robotic system of the plurality of robotic system, wherein
  each stimulus-response pair of the plurality of stimulus-response pairs is indicative of:
   a type of a stimulus, of the plurality of stimuli, that was applied and
   a level of a corresponding response that was generated based on the applied stimulus;
 generating by the server arrangement, one-stimulus multi-response (OSMR) dataset based on the acquired primary information that includes the plurality of stimulus-response pairs; and
 updating, by the server arrangement, a second AI-based system based on the OSMR dataset;
 receiving, by a robotic system of the plurality of robotic systems, an input via a user interface, wherein the input comprises a current health state and a target health state of a user;
 retrieving, by the robotic system, at least one priori stimulus from a knowledge database based on the received input;
 determining, by the robotic system, a set of test stimuli specific for the user based on a combination of the current health state, the target health state, the retrieved at least one priori stimulus, and the updated second AI-based system of the robotic system;

controlling, by the robotic system, a stimulus device of the robotic system to apply the determined set of test stimuli to the user for a first test duration;

determining, by the robotic system, a set of responses discernible on a body of the user from the applied set of test stimuli, wherein the determining of the set of responses discernible on the body is based on a set of external response sensors of the robotic system;

calibrating, by the robotic system, a set of stimulus parameters for the stimulus device based on a combination of the determined set of responses, the current health state, the target health state, and the updated second trained AI-based system; and re-configuring, by the robotic system, the stimulus device with the calibrated set of stimulus parameters to apply a new stimulus to at least a portion of the body of the user for a second duration, wherein the use of the new stimulus shifts at least one condition of the user from the current health state towards the target health state.

* * * * *